(12) United States Patent
Dahmen et al.

(10) Patent No.: US 9,131,685 B2
(45) Date of Patent: Sep. 15, 2015

(54) COMPOSITIONS COMPRISING A STRIGOLACTONE COMPOUND AND A CHITO-OLIGOSACCHARIDE COMPOUND FOR ENHANCED PLANT GROWTH AND YIELD

(75) Inventors: Peter Dahmen, Neuss (DE); Daniela Portz, Vettweiss (DE); Gilbert Spica, Chazay d'Azergues (FR); Jean-Pierre Vors, Saint-foy-les-Lyon (FR)

(73) Assignee: Bayer CropScience AG, Monheim (DE)

( * ) Notice: Subject to any disclaimer, the term of this patent is extended or adjusted under 35 U.S.C. 154(b) by 338 days.

(21) Appl. No.: 13/266,814

(22) PCT Filed: Apr. 27, 2010

(86) PCT No.: PCT/EP2010/055626
§ 371 (c)(1),
(2), (4) Date: Oct. 28, 2011

(87) PCT Pub. No.: WO2010/125065
PCT Pub. Date: Nov. 4, 2010

(65) Prior Publication Data
US 2012/0046169 A1 Feb. 23, 2012

(30) Foreign Application Priority Data
Apr. 28, 2009 (EP) .................................... 09356031

(51) Int. Cl.
| C05F 11/00 | (2006.01) |
| C05F 11/08 | (2006.01) |
| A01P 3/00 | (2006.01) |
| A01N 43/16 | (2006.01) |
| A01P 7/02 | (2006.01) |
| A01N 43/12 | (2006.01) |
| A01N 43/08 | (2006.01) |

(52) U.S. Cl.
CPC ................ *A01N 43/12* (2013.01); *A01N 43/08* (2013.01); *A01N 43/16* (2013.01)

(58) Field of Classification Search
CPC ....... A01N 43/16; A01N 43/08; A01N 43/12; A01N 37/46; A01N 37/50; A01N 43/653; A01N 43/88

USPC ......... 514/55, 414, 473, 470; 504/101; 71/27, 71/6

See application file for complete search history.

(56) References Cited

U.S. PATENT DOCUMENTS

| 2005/0187107 | A1 | 8/2005 | Smith et al. ................... 504/100 |
| 2008/0015109 | A1 | 1/2008 | Smith et al. ................... 504/117 |
| 2008/0318773 | A1* | 12/2008 | Becard et al. ................. 504/100 |

FOREIGN PATENT DOCUMENTS

| EP | WO2005/063784 | * | 7/2005 | ............. C07H 15/20 |
| FR | WO 2005/077177 | * | 4/2005 | ............. A01N 43/12 |
| WO | WO 2005/063784 | | 7/2005 | |
| WO | WO 2008/152092 | | 12/2008 | |

OTHER PUBLICATIONS

Nefkens et al. (J. Agric. Food Chem. vol. 45, No. 6, pp. 2273-2277 1997).*
Umehara et al. (Nature; vol. 455, Sep. 11, 20008; 195-201).*
Nefkens, Gerard H.L., et al.: Synthesis f a Phthaloylglycine-Derived Strigol Analogue and Its Germination Stimulatory Activity toward Seeds of the Parasitic Weeds *Striga hermonthica* and *Orobanche crenata*, J. Agric. Food Chem., 1997, 45, 2273-2277, XP-002296378.
Prithiviraj, B., et al.: "A host-specific bacteria-to-plant signal molecule (Nod factor) enhances germination and early growth of diverse crop plants", Planta (2003) 216:437-445, XP-002288409.
International Search Report issued May 11, 2011 in corresponding International Application No. PCT/EP2010/055626.

\* cited by examiner

*Primary Examiner* — Anna Falkowitz
(74) *Attorney, Agent, or Firm* — Michelle L. Samonek; Adam L. Lunceford

(57) ABSTRACT

The present invention relates to novel active compound combinations comprising a chito-oligosaccharide compound and a strigolactone compound. Compositions of the invention may further comprise a pesticidal active ingredient. The present invention also related to the use of such defined combinations and methods for using them in the control of plant growth and/or yield and/or in the control or prevention of pathogenic or pest damage and/or in order to decreasing the spending on fertilizers.

16 Claims, No Drawings

COMPOSITIONS COMPRISING A STRIGOLACTONE COMPOUND AND A CHITO-OLIGOSACCHARIDE COMPOUND FOR ENHANCED PLANT GROWTH AND YIELD

CROSS-REFERENCE TO RELATED APPLICATION(S)

The present application is a 35 U.S.C. §371 national phase conversion of PCT/EP2010/055626 filed Apr. 27, 2010, which claims priority of European Application No. 09356031.6 filed Apr. 28, 2009. Applicants claim priority to each of the foregoing patent applications. The PCT International Application was published in the English language.

The present invention relates to novel active compound combinations comprising a chito-oligosaccharide compound and a strigolactone compound. Compositions of the invention may further comprise a pesticidal active ingredient. The present invention also related to the use of such defined combinations and methods for using them in the control of plant growth and/or yield and/or in the control or prevention of pathogenic or pest damage and/or in order to decreasing the spending on fertilizers.

It is known that the process of nitrogen fixing by legumes is based on symbiosis between these plants and soil bacteria, the *Rhizobia*. When this rhizobial symbiosis occurs, the legume provides bacteria with energy-rich carbohydrates and some other compounds, while *Rhizobium* supplies the host legume with nitrogen in the form of ammonia. Unlike any plant, *rhizobia* (and some other microorganisms) can fix inert N2 gas from the atmosphere and supply it to the plant as NH4+ which can be utilized by the plant. This symbiosis thus plays a considerable agronomic role. The formation of nitrogen-fixing nodules starts with an exchange of molecular signals, flavonoids secreted by the plant and nodulation factors (Nod factors) synthesized by the bacterium.

More recently, Nod factors have been shown to also enhance the germination, growth and yield of legumes and non-legumes through processes that might be other than nodulation (Prithivaraj et al., Planta 216:437-445, 2003), although the mechanisms involved in such effect are not well understood. Nod factors have also been shown to enhance root development (Olah et al., The plant Journal 44:195-207, 2005), to increase fruiting and/or flowering in strawberries, tomato, hot pepper and ornamental plants as marigold (EP1615499).

Nod factors are lipochito-oligosaccharide compounds (LCOs). The general LCO structure consists of an oligomeric backbone of β-1,4-linked N-acetyl-D-glucosamine residues with an N-linked fatty acyl chain at the non-reducing end.

These lipochito-oligosaccharides (LCO) may be isolated directly from a particular culture of Rhizobiaceae bacterial strains, synthesized chemically, or obtained chemo-enzymatically. Via the latter method, the oligosaccharide skeleton may be formed by culturing of recombinant *Escherichia coli* bacterial strains in a fermenter, and the lipid chain may then be attached chemically.

Apart from these natural LCO compounds, synthetic analogs have been synthetised and shown to be as active as nodulation agent of leguminous plants and/or plant growth stimulators (WO 2005/063784).

Independently to this rhizobial symbiosis between plant roots and soil bacteria, plant roots can also establish symbiotic relationship with arbuscular mycorrhizal (AM) fungi, called mycorrhizal symbiosis. Fungi of the phylum Glomeromycota (AM fungi) penetrate and colonize plant roots, where they differentiate into highly branched structures known as arbuscules and vesicles. AM fungi help plants to capture nutrients such as phosphorus and micronutrients from the soil. More than 80% of lands plants are forming symbiotic associations with AM fungi.

Strigolactones have been identified in the root exudates of a variety of plant species, and have been initially disclosed as compounds capable of stimulating the seed germination of parasitic weed species, especially *Orobanche* sp. and *striga* sp. Several strigolactones have been identified, including strigol, sorgolactone, alectrol, orobanchol (Cook et al., 1972, J Am Chem Soc, 94, 6198-6199; Butler, 1995, Allelopathy: organism, processes and application, 158-168; Hauck et al., 1992, J Plant Physiol, 139, 474-478; Muller et al., 1992, J Plant Growth Regul, 11, 77-84, Siame et al., 1993, J Agr Food Chem, 41, 1486-1491, Yokota et al., 1998, Phytochemistry, 49, 1967-1973).

More recently, it has been shown that strigolactones can stimulate the growth of arbuscular mycorrhizae (AM) fungi (WO 2005/077177).

Natural strigolactones generally possess a chemical structure comprising 4 rings A, B, C, D and share the common configuration indicated below, in which rings A and B can comprises double bond(s) or substituents:

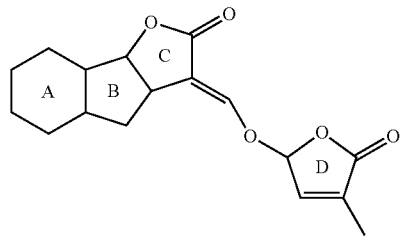

Additionally to these natural occurring compounds, a number of structural analogues have been designated, synthesized and biologically tested on the seed germination or as inducer of hyphal branching.

The connection of the C and D cycles to each other via an enol ether bond seems advantageous for germination stimulation. This C-D configuration is also advantageous for the effect of strigolactones on AM fungi, when modifications in the A and B rings do not appear to affect their ability to induce hyphal branching in AM fungi (Akiyama K. and H. Hayashi H., 2006, Annals of Botany, 97: 925-931). These synthetic compounds, which may be identical to natural strigolactones or derivatives from them, are usually easier to be prepared in large amount than natural compounds extracted from root exsudates. They can therefore overcome a major drawback of the availability of natural compounds and are more suitable for a large scale application.

Described herein is the inventors' surprising discovery that compound combinations comprising a chito-oligosaccharide compound and a strigolactone compound show significant improvement over the individual treatments alone with respect to plant growth, and/or yield of leguminous and non-leguminous plants or crops, and/or decrease of the need for fertilizers.

Additionally, such combinations comprising further a pesticidal active ingredient have demonstrated significant improvement in the combination over the individual treatments alone with respect to pesticidal effect and/or plant growth, vigor or yield of leguminous and non-leguminous plants or crops.

It is always of high-interest in agriculture to use novel mixtures showing a broader scope of activity, or a pesticidal (as for example fungicide, insecticide, nematicide, . . . ) synergistic effect or a synergistic improvement in the plant stand, growth, and yield properties of the plants.

The composition according to the present invention may provide a synergistic effect. This synergistic effect allows a reduction of the chemical substances spread into the environment and a reduction of the cost of the treatment.

The compositions according to the invention have demonstrated significant improvement in the combination over the individual treatments alone with respect to plant growth, vigor or yield of plants or crops, or pesticidal effect.

Accordingly, the present invention provides a composition comprising:

a) a strigolactone derivative of formula (I)

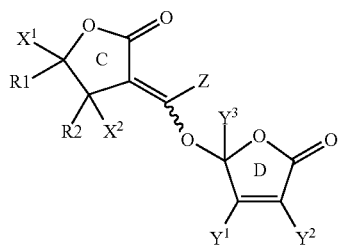

wherein:

$X^1, X^2, Y^1, Y^2, Y^3$ and Z independently represent a hydrogen atom, a halogen atom, a nitro group, a hydroxy group, a cyano group, an amino group, a sulphenyl group, a sulphinyl group, a sulphonyl group, a formyl group, a formyloxy group, a formylamino group, a carbamoyl group, a N-hydroxycarbamoyl group, a carbamate group, substituted or non-substituted (hydroxyimino)-$C_1$-$C_6$-alkyl group, substituted or non-substituted $C_1$-$C_8$-alkyl, substituted or non-substituted tri($C_1$-$C_8$-alkyl)silyl-$C_1$-$C_8$-alkyl, substituted or non-substituted $C_1$-$C_8$-cycloalkyl, substituted or non-substituted tri($C_1$-$C_8$-alkyl)silyl-$C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a substituted or non-substituted $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_2$-$C_8$-alkynyloxy, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-halogenoalkynyloxy having 1 to 5 halogen atoms, substituted or non-substituted $C_1$-$C_8$-alkylcarbonyl, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted di-$C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkylaminocarbonyloxy, substituted or non-substituted di-$C_1$-$C_8$-alkylaminocarbonyloxy, substituted or non-substituted $C_1$-$C_8$-alkyloxycarbonyloxy, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_1$-$C_8$-alkylsulphinyl, substituted or non-substituted $C_1$-$C_8$-halogenoalkylsulphinyl having 1 to 5 halogen atoms, substituted or non-substituted $C_1$-$C_8$-alkylsulphonyl, substituted or non-substituted $C_1$-$C_8$-halogenoalkylsulphonyl having 1 to 5 halogen atoms, substituted or non-substituted $C_1$-$C_8$-alkylaminosulfamoyl, substituted or non-substituted di-$C_1$-$C_8$-alkylaminosulfamoyl, substituted or non-substituted ($C_1$-$C_6$-alkoxyimino)-$C_1$-$C_6$-alkyl, substituted or non-substituted ($C_1$-$C_8$-alkenyloxyimino)-$C_1$-$C_6$-alkyl, substituted or non-substituted ($C_1$-$C_6$-alkynyloxyimino)-$C_1$-$C_6$-alkyl, substituted or non-substituted (benzyloxyimino)-$C_1$-$C_6$-alkyl, substituted or non-substituted $C_1$-$C_8$-alkoxyalkyl, substituted or non-substituted $C_1$-$C_8$-halogenoalkoxyalkyl having 1 to 5 halogen atoms, substituted or non-substituted benzyloxy, substituted or non-substituted benzylsulphenyl, substituted or non-substituted benzylamino, substituted or non-substituted phenoxy, substituted or non-substituted phenylsulphenyl, substituted or non-substituted phenylamino, a substituted or non-substituted or a 4-, 5-, 6- or 7-membered heterocycle comprising up to 4 heteroatoms selected in the list consisting of N, O, S]

R1 and R2 independently represent a hydrogen atom, a halogen atom, a nitro group, a hydroxy group, a cyano group, an amino group, a sulphenyl group, a sulphinyl group, a sulphonyl group, a formyl group, a formyloxy group, a formylamino group, a carbamoyl group, a N-hydroxycarbamoyl group, a carbamate group, substituted or non-substituted (hydroxyimino)-$C_1$-$C_6$-alkyl group, substituted or non-substituted $C_1$-$C_8$-alkyl, substituted or non-substituted tri($C_1$-$C_8$-alkyl)silyl-$C_1$-$C_8$-alkyl, substituted or non-substituted $C_1$-$C_8$-cycloalkyl, substituted or non-substituted tri($C_1$-$C_8$-alkyl)silyl-$C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a substituted or non-substituted $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_2$-$C_8$-alkynyloxy, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-halogenoalkynyloxy having 1 to 5 halogen atoms, substituted or non-substituted $C_1$-$C_8$-alkylcarbonyl, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted di-$C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkylaminocarbonyloxy, substituted or non-substituted di-$C_1$-$C_8$-alkylaminocarbonyloxy, substituted or non-substituted $C_1$-$C_8$-alkyloxycarbonyloxy, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_1$-$C_8$-alkylsulphinyl, substituted or non-substituted $C_1$-$C_8$-halogenoalkylsulphinyl having 1 to 5 halogen atoms, substituted or non-substituted $C_1$-$C_8$-alkylsulphonyl, substituted or non-substituted $C_1$-$C_8$-halogenoalkylsulphonyl having 1 to 5 halogen atoms, substituted or non-substituted $C_1$-$C_8$-alkylaminosulfamoyl, substituted or non-substituted di-$C_1$-$C_8$-alkylaminosulfamoyl, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_8$-alkyl, substituted or non-substituted ($C_1$-$C_8$-alkynyloxyimino)-$C_1$-$C_8$-alkyl, substituted or non-substituted (benzyloxyimino)-$C_1$-$C_6$-alkyl, substituted or non-substituted $C_1$-$C_8$-alkoxyalkyl, substituted or non-substituted $C_1$-$C_8$-halogenoalkoxyalkyl having 1 to 5 halogen atoms, substituted or non-substituted benzyloxy, substituted or non-substituted benzylsulphenyl, substituted or non-substituted benzylamino, substituted or non-substituted phenoxy, substituted or non-substituted phenylsulphenyl, substituted or non-substituted phenylamino, a substituted or non-substituted or a 4-, 5-, 6- or 7-membered heterocycle comprising up to 4 heteroatoms selected in the list consisting of N, O, S]; or R1 and R2 form a saturated or unsaturated, aromatic or non-aromatic, substituted or non-substituted 4- to 7-membered carbocycle; or R1 and R2 form a saturated or unsaturated, aromatic or non-aromatic, substituted or non-substituted 4- to 7-membered carbocycle fused to an other saturated or unsaturated, aromatic or non-aromatic, substituted or non-substituted 4- to 7-membered carbocycle;

as well as salts, N-oxides, metallic complexes, metalloidic complexes and optically active or geometric isomers thereof;

and b) a lipo-chitooligosaccharide compound;

in a (a)/(b) molar ratio of from 0.001 to 1000.

Any of the compounds used in the compositions according to the present invention may also exist in one or more geometric isomeric form depending on the number of double bond within the compound. The invention thus equally relates to any geometric isomer and to any possible mixtures thereof, in any proportion. Geometric isomers can be separated according to any method known per se by the man ordinary skilled in the art.

Any of the compounds used in the compositions according to the present invention wherein a substituent represents a hydroxy group, a sulphenyl group or an amino group can exist in a tautomeric form resulting from the shift of the proton of said hydroxy group, sulphenyl group or amino group respectively. Such tautomeric forms are also part of the present invention.

According to the invention, the following generic terms are generally used with the following meanings:

halogen means fluorine, chlorine, bromine or iodine;
heteroatom can be nitrogen, oxygen or sulphur.

Unless indicated otherwise, a group or a substituent that is substituted according to the invention can be substituted by one or more of the following groups or atoms: a halogen atom, a nitro group, a hydroxy group, a cyano group, an amino group, a sulphenyl group, a sulphinyl group, a sulphonyl group, a formyl group, a formyloxy group, a formylamino group, a carbamoyl group, a N-hydroxycarbamoyl group, a carbamate group, substituted or non-substituted (hydroxyimino)-$C_1$-$C_8$-alkyl group, substituted or non-substituted $C_1$-$C_8$-alkyl, substituted or non-substituted tri($C_1$-$C_8$-alkyl)silyl-$C_1$-$C_8$-alkyl, substituted or non-substituted $C_1$-$C_8$-cycloalkyl, substituted or non-substituted tri($C_1$-$C_8$-alkyl)silyl-$C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_2$-$C_8$-alkenyloxy, substituted or non-substituted $C_2$-$C_8$-alkynyloxy, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted di-$C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkylaminocarbonyloxy, substituted or non-substituted di-$C_1$-$C_8$-alkylaminocarbonyloxy, substituted or non-substituted $C_1$-$C_8$-alkyloxycarbonyloxy, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_1$-$C_8$-alkylsulphinyl, substituted or non-substituted $C_1$-$C_8$-halogenoalkylsulphinyl having 1 to 5 halogen atoms, substituted or non-substituted $C_1$-$C_8$-alkylsulphonyl, substituted or non-substituted $C_1$-$C_8$-halogenoalkylsulphonyl having 1 to 5 halogen atoms, substituted or non-substituted $C_1$-$C_8$-alkylaminosulfamoyl, substituted or non-substituted di-$C_1$-$C_8$-alkylaminosulfamoyl, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_8$-alkyl, substituted or non-substituted ($C_1$-$C_8$-alkynyloxyimino)-$C_1$-$C_8$-alkyl, substituted or non-substituted (benzyloxyimino)-$C_1$-$C_6$-alkyl, substituted or non-substituted $C_1$-$C_8$-alkoxyalkyl, substituted or non-substituted $C_1$-$C_8$-halogenoalkoxyalkyl having 1 to 5 halogen atoms, substituted or non-substituted benzyloxy, substituted or non-substituted benzylsulphenyl, substituted or non-substituted benzylamino, substituted or non-substituted phenoxy, substituted or non-substituted phenylsulphenyl, substituted or non-substituted phenylamino, a substituted or non-substituted or a 4-, 5-, 6- or 7-membered heterocycle comprising up to 4 heteroatoms selected in the list consisting of N, O, S.

A preferred composition according to the invention comprises a compound of formula (I) wherein $X^1$, $X^2$, $Y^1$, $Y^2$, $Y^3$ and Z independently represent a hydrogen atom, a halogen atom, a nitro group, a hydroxy group, a cyano group, a substituted or non-substituted $C_1$-$C_8$-alkyl, a substituted or non-substituted $C_1$-$C_8$-haloalkyl, a substituted or non-substituted $C_1$-$C_8$-alkoxy, or a substituted or non-substituted $C_1$-$C_8$-haloalkoxy.

A more preferred composition according to the invention comprises a compound of formula (I) wherein $X^1$, $X^2$, $Y^1$, $Y^3$ and Z represent a hydrogen atom.

Another more preferred composition according to the invention comprises a compound of formula (I) wherein $Y^2$ represents a substituted or non-substituted $C_1$-$C_8$-alkyl, or a substituted or non-substituted $C_1$-$C_8$-haloalkyl.

Another preferred composition according to the invention comprises a compound of formula (I) wherein R1 and R2 independently represent a hydrogen atom, a halogen atom, a nitro group, a hydroxy group, a cyano group, a substituted or non-substituted $C_1$-$C_8$-alkyl, a substituted or non-substituted $C_1$-$C_8$-haloalkyl, a substituted or non-substituted $C_1$-$C_8$-alkoxy, or a substituted or non-substituted $C_1$-$C_8$-haloalkoxy; or R1 and R2 form a saturated or unsaturated, aromatic or non-aromatic, substituted or non-substituted 4- to 7-membered carbocycle; or R1 and R2 form a saturated or unsaturated, aromatic or non-aromatic, substituted or non-substituted 4- to 7-membered carbocycle fused to an other saturated or unsaturated, aromatic or non-aromatic, substituted or non-substituted 4- to 7-membered carbocycle.

Another more preferred composition according to the invention comprises a compound of formula (I) wherein R1 and R2 form a saturated or unsaturated, aromatic or non-aromatic, substituted or non-substituted 4- to 7-membered carbocycle fused to another saturated or unsaturated, aromatic or non-aromatic, substituted or non-substituted 4- to 7-membered carbocycle.

An even more preferred composition according to the invention comprises a compound of formula (I) wherein R1 and R2 form an unsaturated, non-aromatic, substituted or non-substituted 5-membered carbocycle fused to another unsaturated, aromatic, substituted or non-substituted 6-membered carbocycle.

A preferred composition according to the invention comprises a compound of formula (I) wherein
$X^1$, $X^2$, $Y^1$, $Y^2$, $Y^3$ and Z independently represent a hydrogen atom, a halogen atom, a nitro group, a hydroxy group, a cyano group, a substituted or non-substituted $C_1$-$C_8$-alkyl, a substituted or non-substituted $C_1$-$C_8$-haloalkyl, a substituted or non-substituted $C_1$-$C_8$-alkoxy, or a substituted or non-substituted $C_1$-$C_8$-haloalkoxy; and R1 and R2 form an unsaturated, non-aromatic, substituted or non-substituted 5-membered carbocycle fused to another unsaturated, aromatic, substituted or non-substituted 6-membered carbocycle.

An even preferred composition according to the invention comprises a compound of formula (I) wherein
$X^1$, $X^2$, $Y^1$, $Y^3$ and Z independently represent a hydrogen atom;

$Y^2$ represents a substituted or non-substituted $C_1$-$C_8$-alkyl or a substituted or non-substituted $C_1$-$C_8$-haloalkyl; and R1 and R2 form an unsaturated, non-aromatic substituted or non-substituted 5-membered carbocycle fused to another unsaturated, aromatic, substituted or non-substituted 6-membered carbocycle.

A preferred composition according to the invention comprises a compound of formula (I) selected in the list consisting of:

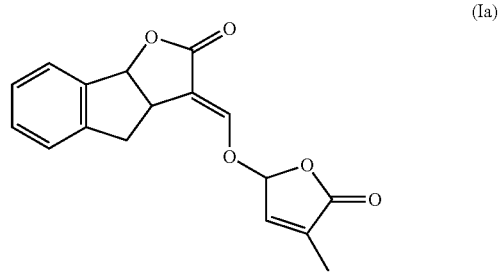

(Ia)

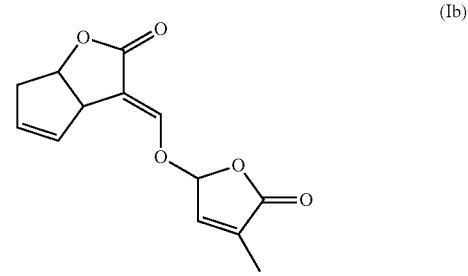

(Ib)

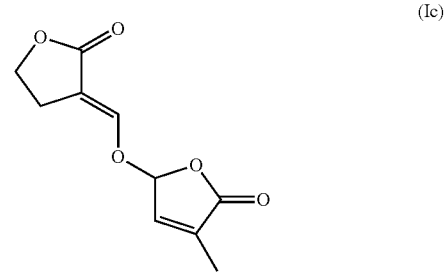

(Ic)

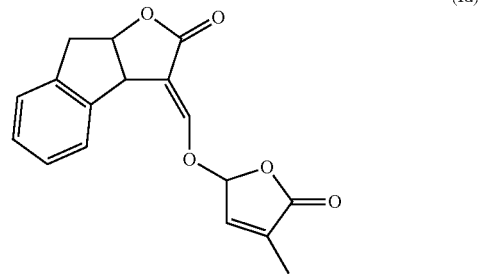

(Id)

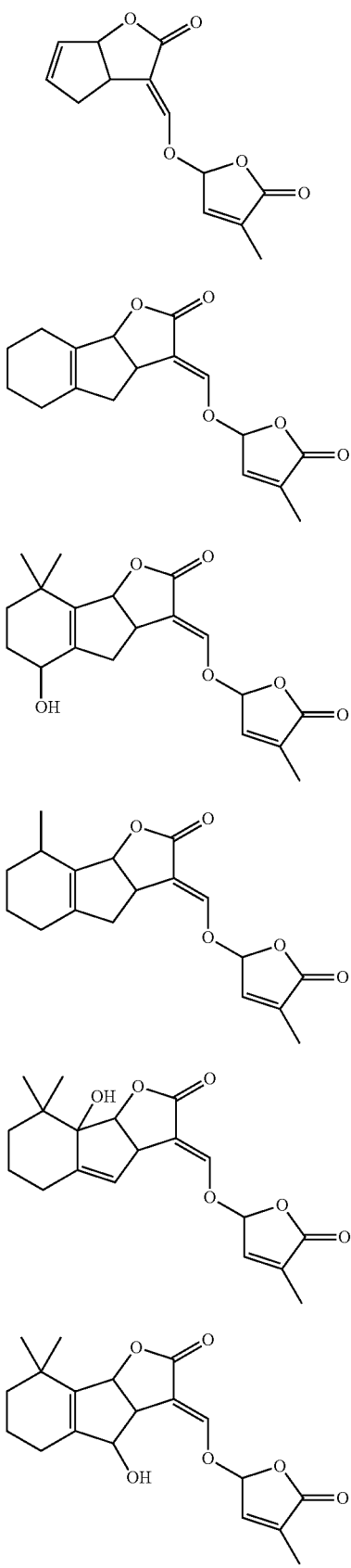

(Ie)
(If)
(Ig)
(Ih)
(Ij)
(Ik)

According to another aspect, the present invention provides a composition comprising:

a) a compound of formula (II)

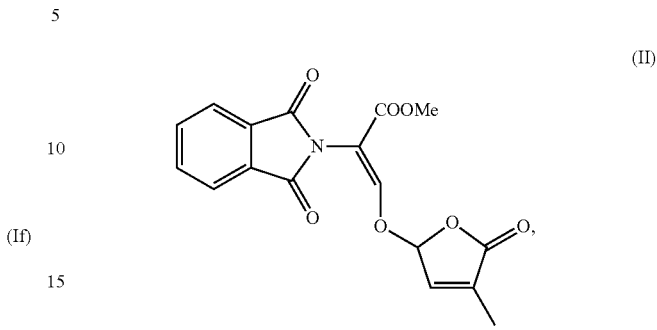

and b) a lipo-chitooligosaccharide compound;

in a (a)/(b) molar ratio of from 0.001 to 1000

Protocols to synthesise the compound of formula (I) and (II) according to the invention are well known by those skilled in the art (Bouwmeester et al, 2003, Current opinion in Plant Biology 6: 358-364; Mangnus et al., 1992, J. Agric. Food Chem. 40(6):697-700; Frischmuth et al, 1991, Tetrahedron 47:9793-9806; Mwakaboko A. S., 2003, "Synthesis and biological evaluation of new strigolactone analogues as germination stimulants for the seeds of the parasitic weeds *Striga* and *Orobanche* spp", Doctoral thesis, http://webdoc.ubn.kun.nl/mono/m/mwakaboko_a/syntanbie.pdf).

As an example, Mwakaboko A. S. discloses in his thesis the synthesis of some structurally modified strigolactones (chapter 8 & 9).

In the meaning of the invention, a lipo-chitooligosaccharide compound is a compound having the general LCO structure, i.e. an oligomeric backbone of β-1,4-linked N-acetyl-D-glucosamine residues with a N-linked fatty acyl chain at the non-reducing end, as described in U.S. Pat. No. 5,549,718; U.S. Pat. No. 5,646,018; U.S. Pat. No. 5,175,149; and U.S. Pat. No. 5,321,011.

This basic structure may contain modifications or substitutions found in naturally occurring LCO's, such as those described in Spaink, Critical Reviews in Plant Sciences 54: 257-288, 2000; D'Haeze and Holsters, Glycobiology 12: 79R-105R, 2002.

Naturally occurring LCO's are defined as compounds which can be found in nature. For the purpose of the invention, said naturally occurring LCO's may be isolated from the natural organism, or can be a partial or totally synthetic version of said naturally occurring LCO.

This basic structure may also contain modifications or substitutions which have not been found so far in naturally occurring LCO's. Examples of such analogs for which the conjugated amide bond is mimicked by a benzamide bond or which contain a function of benzylamine type are the following compounds of formula (I) which are described in WO2005/063784 and WO2008/071672, the content of which is incorporated herein by reference.

In a particular embodiment of the invention, lipo-chitooligosaccharide compounds according to the invention encompasse compounds of formula (III):

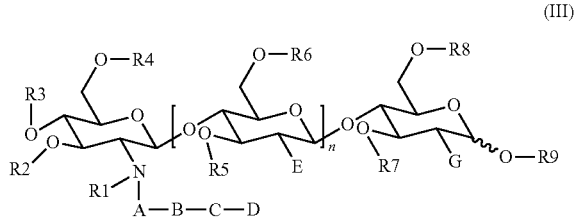

(III)

in which n represents 1, 2 or 3;

A represents a substituent chosen from —C(O)—, —C(S)—, —CH2-, —CHR10-, —CR10R11—, —C(O)O—, —C(O)S—, —C(S)O—, —C(S)S—, —C(O)NH—, —C(NH)NH— and —C(S)NH—;

B represents
an arylene;
a heteroarylene comprising 1 or 2 hetero atoms chosen from nitrogen, oxygen and sulfur;
a naphthylene;
a heteronaphthylene comprising 1 or 2 hetero atoms chosen from nitrogen, oxygen and sulfur;
a divalent radical derived from 2 fused aromatic rings of 5 or 6 atoms each;
a divalent radical derived from 2 fused aromatic or heteroaromatic rings of 5 or 6 atoms each, comprising 1 or 2 hetero atoms chosen from nitrogen, oxygen and sulfur;
a biphenylene;
or a heterobiphenylene comprising 1 or 2 hetero atoms chosen from nitrogen, oxygen and sulfur;

these groups possibly being substituted with one or two substituents R12 and R13 chosen, independently of each other, from halogen, CN, C(O)OR14, C(O)NR15R16, CF3, OCF3, —NO2, N3, OR14, SR14, NR15R16 and C1-6-alkyl;

C represents a substituent chosen from —O—, —S—, —CH2-, —CHR17-, —CR17R18- and —NR19;

D represents a linear or branched, saturated or unsaturated hydrocarbon-based chain containing from 2 to 20 carbon atoms;

E and G represent, independently of each other, a substituent chosen from H, OH, OR20, NH2 and NHR20;

R1 represents a substituent chosen from H, C1-6-alkyl, C(O)H and C(O)CH3;

R2, R3, R6, R14, R15, R16 and R19 represent, independently of each other, a substituent chosen from H, C1-6-alkyl, C(O)C1-6-alkyl, —C(S)C1-6-alkyl, —C(O)OC1-6-alkyl, —C(O)NH2, —C(S)NH2, —C(NH)NH2, —C(O)NHC1-6-alkyl, —C(S)NHC1-6-alkyl and —C(NH)NHC1-6-alkyl;

R4 represents a substituent chosen from H, C1-6-alkyl and R21;

R5 represents a substituent chosen from H, C1-6-alkyl, fucosyl and R22;

R7 represents a substituent chosen from H, C1-6-alkyl, arabinosyl and R23;

R8 represents a substituent chosen from H, C1-6-alkyl, fucosyl, methylfucosyl, sulfofucosyl, acetylfucosyl, arabinosyl, SO3H, SO3Li, SO3Na, SO3K, SO3N(C1-8alkyl)4 and R24;

R9 represents a substituent chosen from H, C1-6-alkyl, mannose, glycerol and R25;

R10, R11, R17 and R18 represent, independently of each other, a substituent chosen from C1-6-alkyl and F;

R20, R21, R22, R23, R24 and R25 represent, independently of each other, a substituent chosen from C(O)C1-6-alkyl, —C(S)C1-6-alkyl, —C(O)OC1-6-alkyl, —C(O)NH2, —C(S)NH2, —C(NH)NH2, —C(O)NHC1-6-alkyl, —C(S)NHC1-6-alkyl and —C(NH)NHC1-6-alkyl;

and also the possible geometrical and/or optical isomers, enantiomers and/or diastereoisomers, tautomers, salts, N-oxides, sulfoxides, sulfones, metal or metalloid complexes thereof, which are agriculturally acceptable. Among the compounds defined above, the most important compounds are the salts, more particularly the lithium, sodium, potassium or tetraalkylammonium salts;

Among these compounds of formula (III), these ones which have one or other of the following characteristics, taken separately or in combination, may be particularly advantageous:

n represents 2 or 3;
A represents —C(O)— or —CH2—;
B represents a phenylene;
C represents —O—;
D represents a linear, saturated or unsaturated hydrocarbon-based chain containing from 3 to 17 carbon atoms;
E and G represent NHC(O)CH3;
$R^1$ represents H, CH3 or C(O)CH3;
$R^2$, $R^3$, $R^5$, $R^6$, $R^7$ and $R^9$ represent H;
$R^4$ represents H, C(O)CH3 or C(O)NH2;
$R^8$ represents H, SO3H, SO3Li, SO3Na, SO3K, SO3N(C1-8 alkyl)4, fucosyl or methylfucosyl.

Among these compounds, the ones that are preferred are those of formula (III) simultaneously having the following characteristics:

n represents 2 or 3;
A represents —C(O)— or —CH2—;
E and G represent NHC(O)CH3;
$R^1$ represents H, CH3 or C(O)CH3;
$R^2$, $R^3$, $R^5$, $R^6$, $R^7$ and $R^9$ represent H;
$R^4$ represents H, C(O)CH3 or C(O)NH2;
$R^8$ represents H, SO3H, SO3Li, SO3Na, SO3K, SO3N(C1-8 alkyl)4, fucosyl or methylfucosyl; even more preferably, those simultaneously having the following characteristics:

n represents 2 or 3;
A represents —C(O)— or —CH2—;
D represents a linear, saturated or unsaturated hydrocarbon-based chain containing from 3 to 17 carbon atoms;
E and G represent NHC(O)CH3;
$R^1$ represents H, CH3 or C(O)CH3;
$R^2$, $R^3$, $R^5$, $R^6$, $R^7$ and $R^9$ represent H;
$R^4$ represents H, C(O)CH3 or C(O)NH2;
$R^8$ represents H, SO3H, SO3Li, SO3Na, SO3K, SO3N(C1-8 alkyl)4, fucosyl or methylfucosyl;

and most preferably the compounds of formula (III) simultaneously having the following characteristics:

n represents 2 or 3;
A represents —C(O)— or —CH2—;
C represents —O—;
D represents a linear, saturated or unsaturated hydrocarbon-based chain containing from 3 to 17 carbon atoms;
E and G represent NHC(O)CH3;
$R^1$ represents H, CH3 or C(O)CH3;
$R^2$, $R^3$, $R^5$, $R^6$, $R^7$ and $R^9$ represent H;
$R^4$ represents H, C(O)CH3 or C(O)NH2;
$R^8$ represents H, SO3H, SO3Li, SO3Na, SO3K, SO3N(C1-8 alkyl)4, fucosyl or methylfucosyl.

Among these preferred compounds, mention may be made of the compounds of formula (III) simultaneously having the following characteristics:

n represents 2 or 3;
A represents —C(O)— or —CH$_2$—;
B represents a phenylene;
C represents —O—;
D represents a linear hydrocarbon-based chain containing 11 carbons, which is saturated, or unsaturated between carbons 4 and 5;
E and G represent NHC(O)CH$_3$;
R$^1$ represents H, CH$_3$ or C(O)CH$_3$;
R$^2$, R$^3$, R$^5$, R$^6$, R$^7$ and R$^9$ represent H;
R$^4$ represents H, C(O)CH$_3$ or C(O)NH$_2$;
R$^8$ represents H, SO$_3$H, SO$_3$Li, SO$_3$Na, SO$_3$K, SO$_3$N(C$_{1-8}$ alkyl)$_4$, fucosyl or methylfucosyl.

As examples of compositions according to the invention that are particularly advantageous and preferred, mention may be made of the compositions comprising a compound corresponding to one of the following formulae:

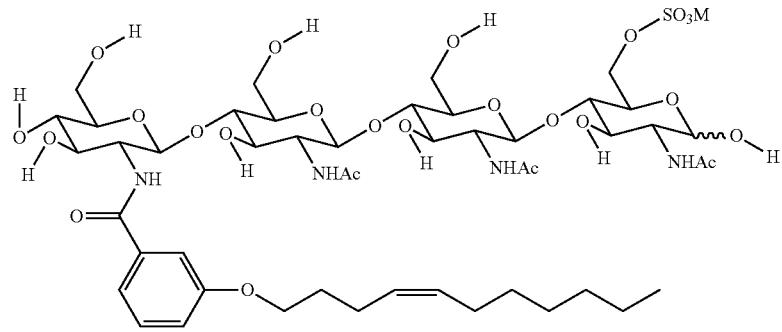

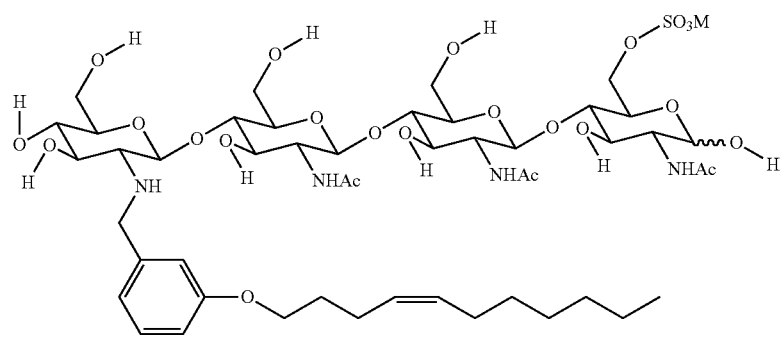

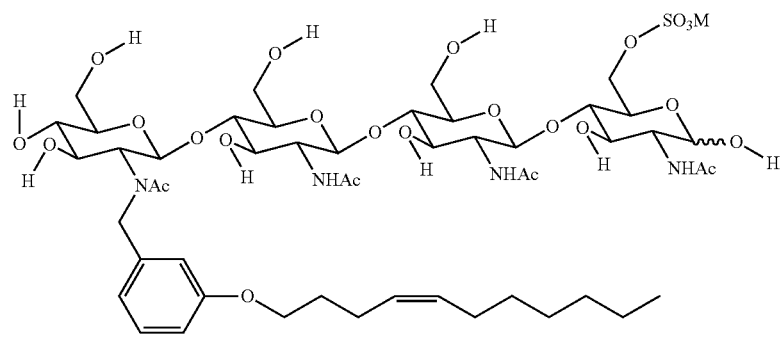

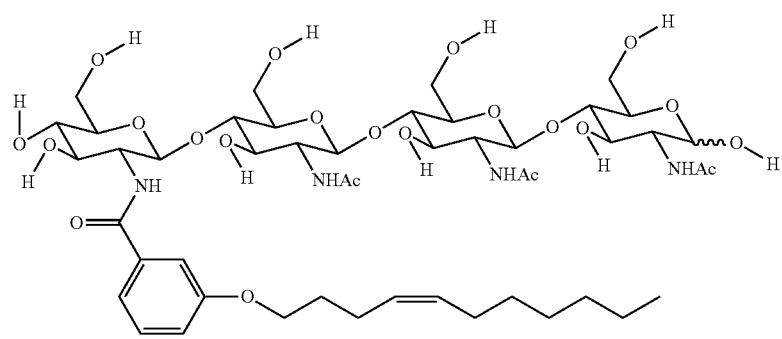

-continued
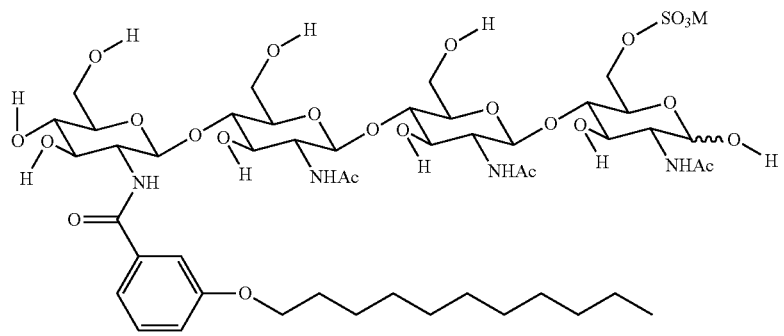
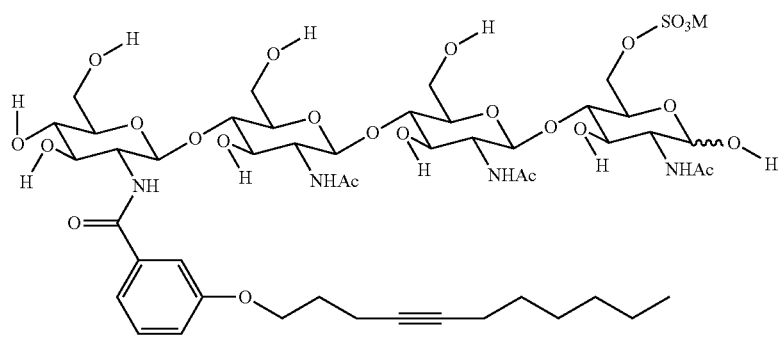
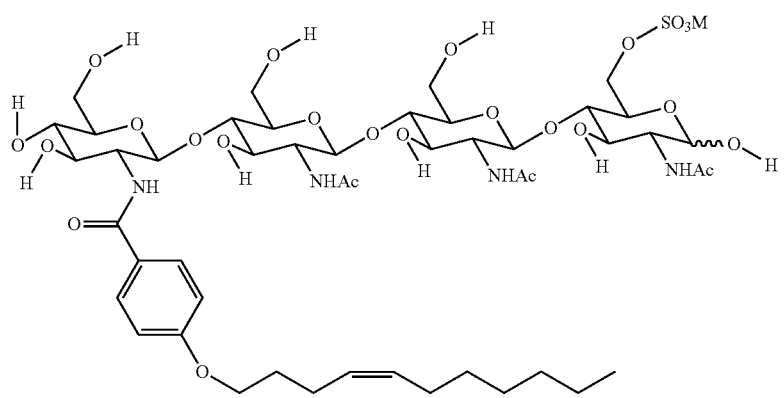
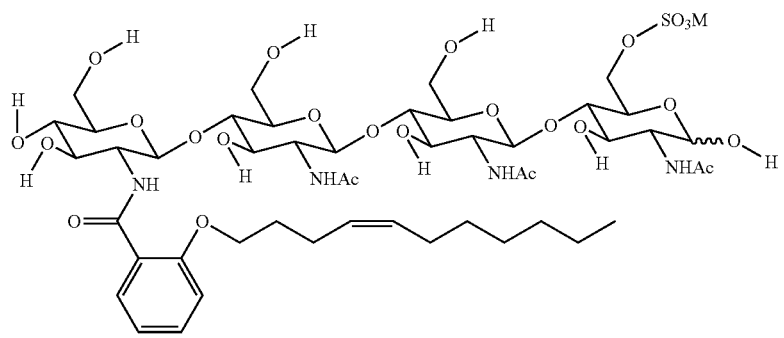

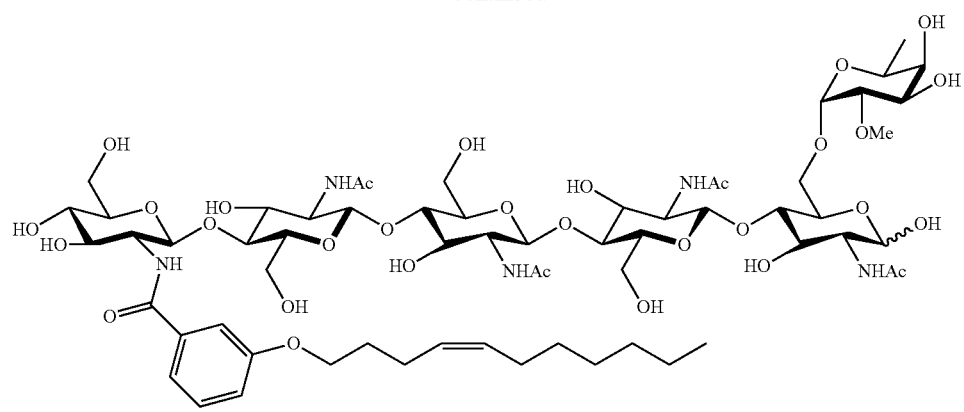
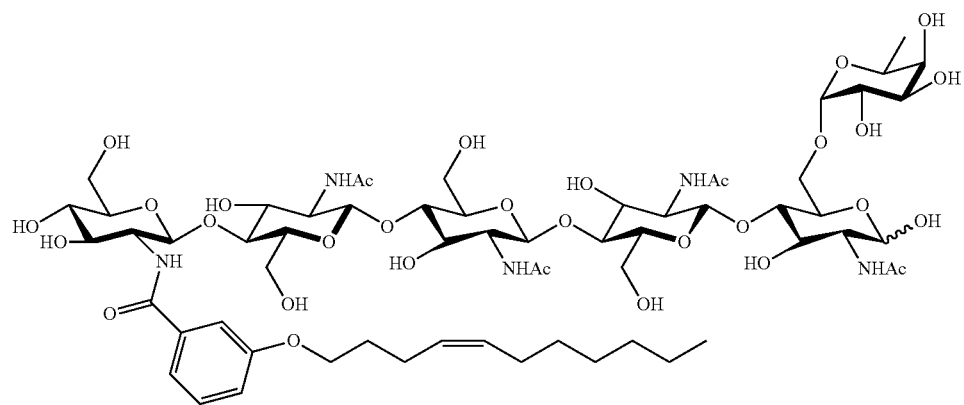
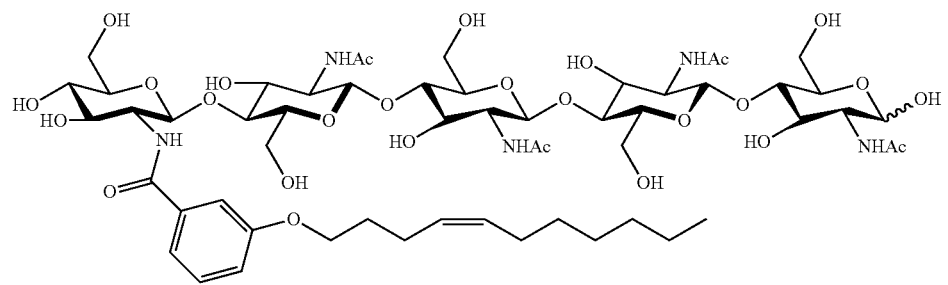
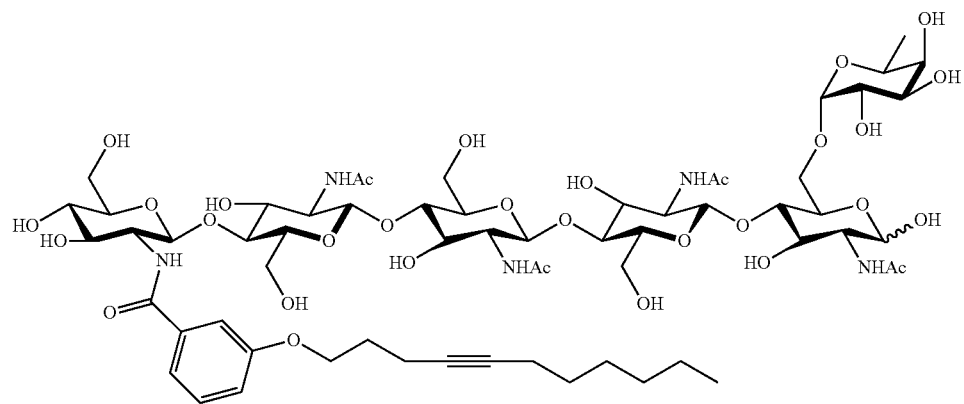

-continued
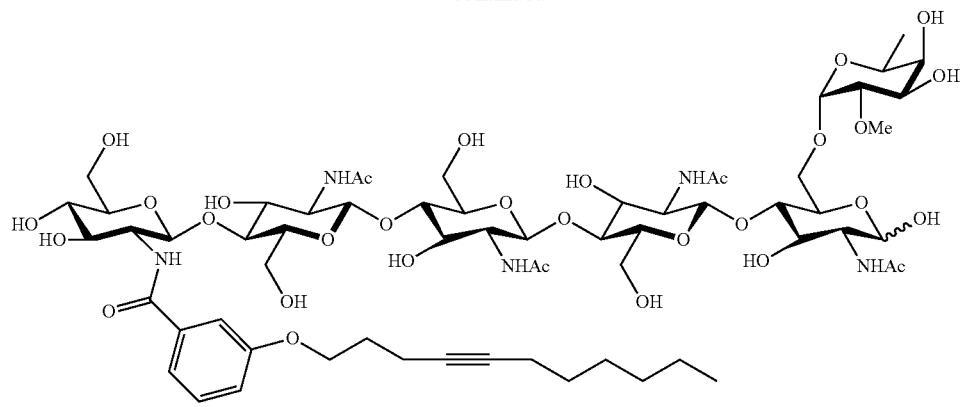
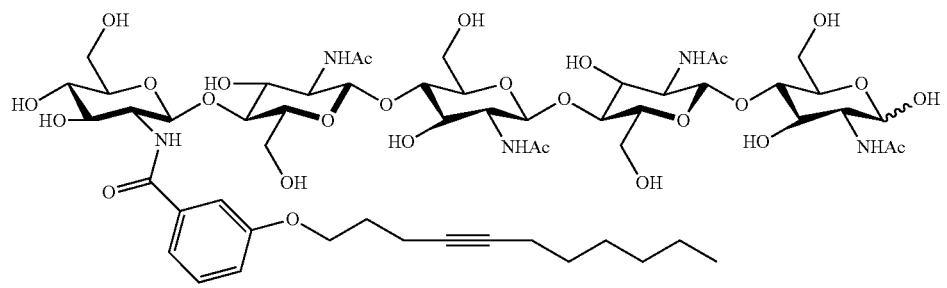
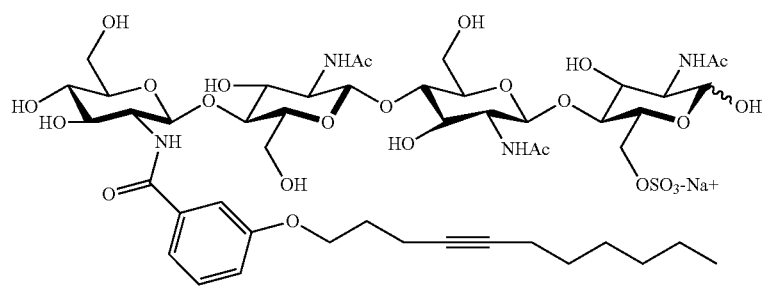
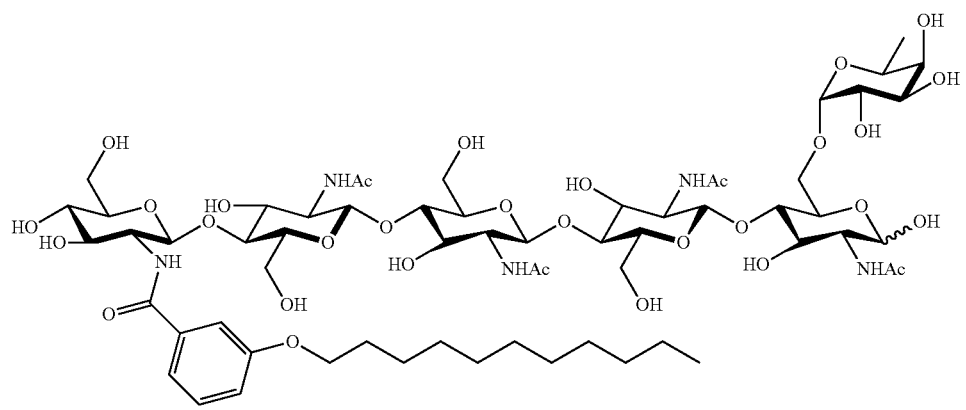

-continued

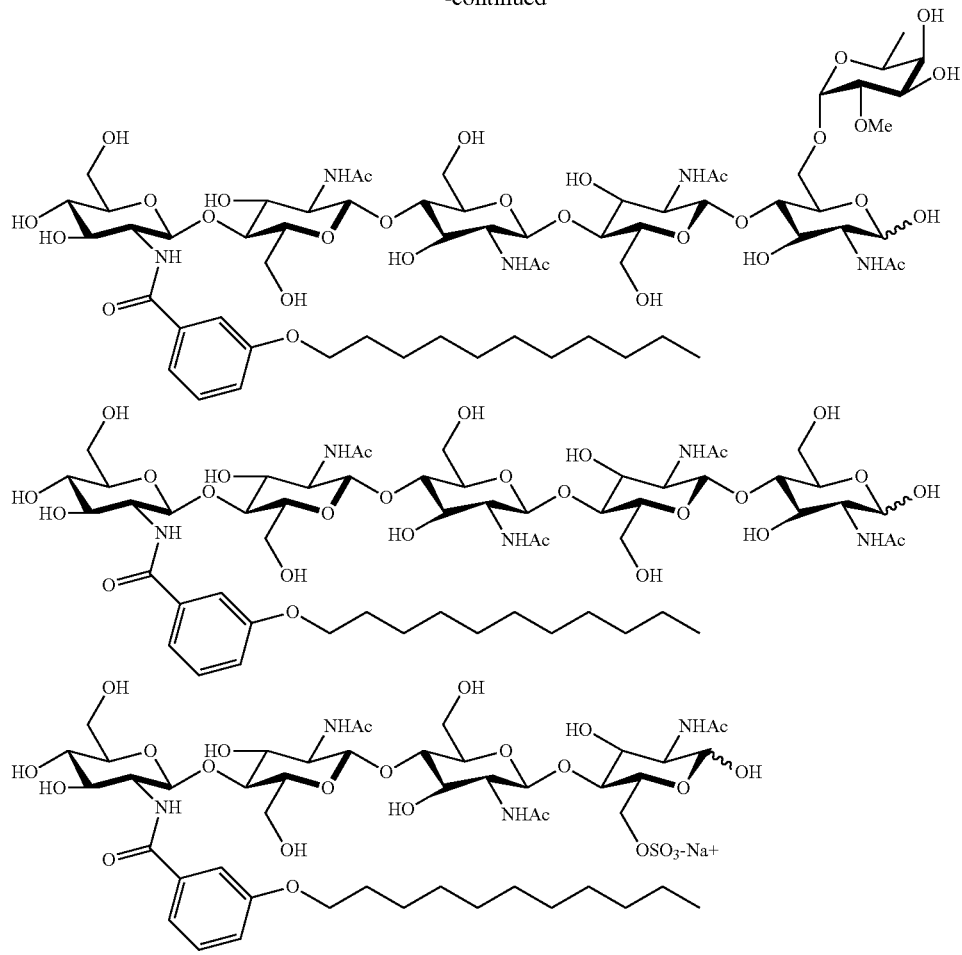

in which, when it is present, M represents a cation chosen from $H^+$, $Li^+$, $Na^+$, $K^+$ and $(C_{1-8}alkyl)_4N^+$.

The LCO's compounds may be isolated directly from a particular culture of Rhizobiaceae bacterial strains, synthesized chemically, or obtained chemo-enzymatically. Via the latter method, the oligosaccharide skeleton may be formed by culturing of recombinant bacterial strains, such as *Escherichia coli*, in a fermenter, and the lipid chain may then be attached chemically.

LCO's used in embodiments of the invention may be recovered from natural Rhizobiaceae bacterial strains that produce LCO's, such as strains of *Azorhizobium, Bradyrhizobium* (including *B. japonicum*), *Mesorhizobium, Rhizobium* (including *R. leguminosarum*), *Sinorhizobium* (including *S. meliloti*), or from bacterial strains genetically engineered to produce LCO's. These methods are known in the art and have been described, for example, in U.S. Pat. Nos. 5,549,718 and 5,646,018, which are incorporated herein by reference.

Within the legume family, specific genera and species of *rhizobium* develop a symbiotic nitrogen-fixing relationship with a specific legume host. These plant host/*rhizobia* combinations are described in Hungria and Stacey, Soil Biol. Biochem. 29: 819-830, 1997, which also lists specific LCO structures that are produced by the different rhizobial species. However, LCO specificity is only required to establish nodulation in legumes. It is not necessary to match LCO's and plant species to stimulate plant growth and/or crop yield when treating seeds or foliage of a legume or non-legume with LCO's.

LCO's may be utilized in various forms of purity and may be used alone or with *rhizobia*. Methods to provide only LCO's include simply removing the rhizobial cells from a mixture of LCOs and *rhizobia*, or continuing to isolate and purify the LCO molecules through LCO solvent phase separation followed by HPLC chromatography as described by Lerouge, et. al (U.S. Pat. No. 5,549,718). Purification can be enhanced by repeated HPLC, and the purifed LCO molecules can be freeze-dried for long-term storage. This method is acceptable for the production of LCO's from all genera and species of the Rhizobiaceae.

Commercial products containing LCO's are available, such as OPTIMIZE® (EMD Crop BioScience).

LCO compounds, which can be identical or not to naturally occurring LCO's, may also be obtained by chemical synthesis and/or through genetic engineering. Synthesis of precursor oligosaccharide molecules for the construction of LCO by genetically engineered organisms is disclosed in Samain et al., Carbohydrate Research 302: 35-42, 1997.

Preparation of numerous LCOs compounds wherein the oligosaccharide skeleton is obtained by culturing recombinant bacterial strains, such as recombinant *Escherichia coli* cells harboring heterologous gene from *rhizobia*, and wherein the lipid chain is chemically attached is disclosed in WO2005/063784 and WO2008/07167, the content of which is incorporated herein by reference.

Compositions according to the invention comprises
a) a strigolactone derivative of formula (I) or (II) as herein described; and
b) a lipo-chitooligosaccharide compound;
in a (a)/(b) molar ratio of from 0.001 to 1000.

Preferably, (a)/(b) molar ratio is of from 0.01 to 500, more preferably from 0.02 to 250, even more preferably of from 0.05 to 100.

A man of ordinary skill in the art would be able to determine the adequate ratios according to the methods of application and to the compounds.

In one embodiment of the invention, the composition may be prepared by combining one or more strigolactone compound(s) and one or more LCO compound(s) in an agriculturally appropriate solvent. An "effective amount" of the composition is an amount that increases plant growth or crop yield when compared with the growth or crop yield of plants or seeds that have not been treated with the composition. For example, strigolactone concentration and LCO concentration in the composition may range independently from $10^{-4}$ M to $10^{-12}$ M, preferably from $10^{-5}$ to $10^{-10}$ M. Strigolactone and LCO components may consist of purified or partly purified compounds. The agriculturally appropriate solvent is preferably an aqueous solvent, such as water. It may be appropriate to solubilize the compounds in a small volume of organic solvent as acetone, and then to dilute with water.

Active ingredients concentration in the composition generally corresponds directly or after dilution to the use rate for this particular active ingredient. The use rate for strigolactone compounds is generally from 1 µg to 1 g/ha; the use rate for LCO compounds is generally from 1 µg to 100 g/ha.

Although it is efficient and convenient to combine and apply the strigolactone and LCO components in a single mixture, in one embodiment of the invention the strigolactone and LCO components may be applied separately and sequentially in either order. Other additives that may be applied either simultaneously or sequentially include fertilizers (e.g., calcium, nitrogen, potassium, phosphorous) and micronutrients (e.g., copper, aluminum, magnesium, manganese, and zinc ions).

The composition may be applied to monocot or dicot plants, including legumes and non-legumes. In one embodiment, the composition is applied to field-grown plants. In another embodiment, the composition is applied to greenhouse-grown plants. For example, the composition may be applied to seeds or foliage of legumes, such as soybeans, peas, chickpeas, dry beans, peanuts, clover, alfalfa, and of non-legumes such as corn, cotton, rice, tomatoes, canola, wheat, barley, sugar beet, and grass. In general, for seed treatment, the composition is applied to seeds in a single application, and the seeds may be planted immediately or stored before planting. The composition may be applied to foliage. Foliar application generally consists of spraying the composition on the plant foliage one or more times during the growing period.

The term "plant" as used herein includes tubers, roots, stems, leaves, flowers, and fruits. The composition may be applied directly to seeds or plants or may be placed in soil in the vicinity of a seed or plant prior to or at the time of planting. In a preferred embodiment, the composition is sprayed on seeds, tubers, or foliage.

Seedlings, as well as more mature plants, may be treated. Flowers and fruits may also be treated by spraying. Roots of transplants may be sprayed or dipped in the composition prior to planting.

The composition according to the present invention may further comprise a supplementation with different inoculum sources as for example arbuscular mycorrhizal fungi (AMF), *Rhizobia* or other plant growth promoting bacteria. Said supplementation may be applied simultaneously to the LCO component, to the strigolactone component, to the LCO and strigolactone components or sequentially. AMF could be for example *Glomus* sp., *Gigaspora* sp., or other fungi from the group Glomeromycota, while plant growth promoting bacteria others than *Rhizobia* could be for example *Azospirillum* sp., *Bacillus* sp.

In another embodiment of the invention, the composition further comprises a pesticidal active ingredient. Examples of pesticides useful in compositions include fungicides, insecticides, nematicides, acaricides and molluscicides.

Examples of suitable fungicide mixing partners may be selected in the following lists:
(1) Inhibitors of the ergosterol biosynthesis, for example (1.1) aldimorph (1704-28-5), (1.2) azaconazole (60207-31-0), (1.3) bitertanol (55179-31-2), (1.4) bromuconazole (116255-48-2), (1.5) cyproconazole (113096-99-4), (1.6) diclobutrazole (75736-33-3), (1.7) difenoconazole (119446-68-3), (1.8) diniconazole (83657-24-3), (1.9) diniconazole-M (83657-18-5), (1.10) dodemorph (1593-77-7), (1.11) dodemorph acetate (31717-87-0), (1.12) epoxiconazole (106325-08-0), (1.13) etaconazole (60207-93-4), (1.14) fenarimol (60168-88-9), (1.15) fenbuconazole (114369-43-6), (1.16) fenhexamid (126833-17-8), (1.17) fenpropidin (67306-00-7), (1.18) fenpropimorph (67306-03-0), (1.19) fluquinconazole (136426-54-5), (1.20) flurprimidol (56425-91-3), (1.21) flusilazole (85509-19-9), (1.22) flutriafol (76674-21-0), (1.23) furconazole (112839-33-5), (1.24) furconazole-cis (112839-32-4), (1.25) hexaconazole (79983-71-4), (1.26) imazalil (60534-80-7), (1.27) imazalil sulfate (58594-72-2), (1.28) imibenconazole (86598-92-7), (1.29) ipconazole (125225-28-7), (1.30) metconazole (125116-23-6), (1.31) myclobutanil (88671-89-0), (1.32) naftifine (65472-88-0), (1.33) nuarimol (63284-71-9), (1.34) oxpoconazole (174212-12-5), (1.35) paclobutrazol (76738-62-0), (1.36) pefurazoate (101903-30-4), (1.37) penconazole (66246-88-6), (1.38) piperalin (3478-94-2), (1.39) prochloraz (67747-09-5), (1.40) propiconazole (60207-90-1), (1.41) prothioconazole (178928-70-6), (1.42) pyributicarb (88678-67-5), (1.43) pyrifenox (88283-41-4), (1.44) quinconazole (103970-75-8), (1.45) simeconazole (149508-90-7), (1.46) spiroxamine (118134-30-8), (1.47) tebuconazole (107534-96-3), (1.48) terbinafine (91161-71-6), (1.49) tetraconazole (112281-77-3), (1.50) triadimefon (43121-43-3), (1.51) triadimenol (89482-17-7), (1.52) tridemorph (81412-43-3), (1.53) triflumizole (68694-11-1), (1.54) triforine (26644-46-2), (1.55) triticonazole (131983-72-7), (1.56) uniconazole (83657-22-1), (1.57) uniconazole-p (83657-17-4), (1.58) viniconazole (77174-66-4), (1.59) voriconazole (137234-62-9), (1.60) 1-(4-chlorophenyl)-2-(1H-1,2,4-triazol-1-yl)cycloheptanol (129586-32-9), (1.61) methyl 1-(2,2-dimethyl-2,3-dihydro-1H-inden-1-yl)-1H-imidazole-5-carboxylate (110323-95-0), (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide and (1.64) O-[1-(4-methoxyphenoxy)-3,3-dimethylbutan-2-yl] 1H-imidazole-1-carbothioate (111226-71-2).
(2) inhibitors of the respiratory chain at complex I or II, for example (2.1) bixafen (581809-46-3), (2.2) boscalid (188425-85-6), (2.3) carboxin (5234-68-4), (2.4) diflumetorim (130339-07-0), (2.5) fenfuram (24691-80-3), (2.6) fluopyram (658066-35-4), (2.7) flutolanil (66332-96-5), (2.8) fluxapyroxad (907204-31-3), (2.9) furametpyr (123572-88-3), (2.10) furmecyclox (60568-05-0), (2.11) isopyrazam (mixture of syn-epimeric racemate 1RS,4SR,9RS and anti-epimeric racemate 1RS,4SR,9SR) (881685-58-1), (2.12) isopyrazam (anti-epimeric racemate 1RS,4SR,9SR), (2.13) isopyrazam (anti-epimeric enantiomer 1R,4S,9S), (2.14) isopyrazam (anti-epimeric enantiomer 1S,4R,9R), (2.15) isopyrazam (syn epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil (55814-41-0), (2.19) oxycarboxin (5259-88-1), (2.20) penflufen (494793-67-8), (2.21) penthiopyrad (183675-82-3), (2.22) sedaxane (874967-67-6), (2.23) thifluzamide (130000-40-7), (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide (1092400-95-7) (WO 2008148570) and salts thereof.

(3) inhibitors of the respiratory chain at complex III, for example (3.1) ametoctradin (865318-97-4), (3.2) amisulbrom (348635-87-0), (3.3) azoxystrobin (131860-33-8), (3.4) cyazofamid (120116-88-3), (3.5) dimoxystrobin (141600-52-4), (3.6) enestroburin (238410-11-2) (WO 2004/058723), (3.7) famoxadone (131807-57-3) (WO 2004/058723), (3.8) fenamidone (161326-34-7) (WO 2004/058723), (3.9) fluoxastrobin (361377-29-9) (WO 2004/058723), (3.10) kresoxim-methyl (143390-89-0) (WO 2004/058723), (3.11) metominostrobin (133408-50-1) (WO 2004/058723), (3.12) orysastrobin (189892-69-1) (WO 2004/058723), (3.13) picoxystrobin (117428-22-5) (WO 2004/058723), (3.14) pyraclostrobin (175013-18-0) (WO 2004/058723), (3.15) pyrametostrobin (915410-70-7) (WO 2004/058723), (3.16) pyraoxystrobin (862588-11-2) (WO 2004/058723), (3.17) pyribencarb (799247-52-2) (WO 2004/058723), (3.18) trifloxystrobin (141517-21-7) (WO 2004/058723), (3.19) (2E)-2-(2-{[6-(3-chloro-2-methylphenoxy)-5-fluoropyrimidin-4-yl]oxy}phenyl)-2-(methoxyimino)-N-methylethanamide (WO 2004/058723), (3.20) (2E)-2-(methoxyimino)-N-methyl-2-(2-{[({(1E)-1-[3-(trifluoromethyl)phenyl]ethylidene}amino)oxy]methyl}phenyl)ethanamide (WO 2004/058723) and salts thereof, (3.21) (2E)-2-(methoxyimino)-N-methyl-2-{2-[(E)-({1-[3-(trifluoromethyl)phenyl]ethoxy}imino)methyl]phenyl}ethanamide (158169-73-4), (3.22) (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide (326896-28-0), (3.23) (2E)-2-{2-[({[(2E,3E)-4-(2,6-dichlorophenyl)but-3-en-2-ylidene]amino}oxy)methyl]phenyl}-2-(methoxyimino)-N-methylethanamide, (3.24) 2-chloro-N-(1,1,3-trimethyl-2,3-dihydro-1H-inden-4-yl)pyridine-3-carboxamide (119899-14-8), (3.25) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.26) methyl (2E)-2-{2-[({cyclopropyl[(4-methoxyphenyl)imino]methyl}sulfanyl)methyl]phenyl}-3-methoxyprop-2-enoate (149601-03-6), (3.27) N-(3-ethyl-3,5,5-trimethylcyclohexyl)-3-(formylamino)-2-hydroxybenzamide (226551-21-9), (3.28) 2-{2-[(2,5-dimethylphenoxy)methyl]phenyl}-2-methoxy-N-methylacetamide (173662-97-0), (3.29) (2R)-2-{2-[(2,5-dimethylphenoxy)methyl]phenyl}-2-methoxy-N-methylacetamide (394657-24-0) and salts thereof.

(4) Inhibitors of the mitosis and cell division, for example (4.1) benomyl (17804-35-2), (4.2) carbendazim (10605-21-7), (4.3) chlorfenazole (3574-96-7), (4.4) diethofencarb (87130-20-9), (4.5) ethaboxam (162650-77-3), (4.6) fluopicolide (239110-15-7), (4.7) fuberidazole (3878-19-1), (4.8) pencycuron (66063-05-6), (4.9) thiabendazole (148-79-8), (4.10) thiophanate-methyl (23564-05-8), (4.11) thiophanate (23564-06-9), (4.12) zoxamide (156052-68-5), (4.13) 5-chloro-7-(4-methylpiperidin-1-yl)-6-(2,4,6-trifluorophenyl)[1,2,4]triazolo[1,5-a]pyrimidine (214706-53-3), (4.14) 3-chloro-5-(6-chloropyridin-3-yl)-6-methyl-4-(2,4,6-trifluorophenyl)pyridazine (1002756-87-7) and salts thereof.

(5) Compounds capable to have a multisite action, like for example (5.1) bordeaux mixture (8011-63-0), (5.2) captafol (2425-06-1), (5.3) captan (133-06-2) (WO 02/12172), (5.4) chlorothalonil (1897-45-6), (5.5) copper hydroxide (20427-59-2), (5.6) copper naphthenate (1338-02-9), (5.7) copper oxide (1317-39-1), (5.8) copper oxychloride (1332-40-7), (5.9) copper (2+) sulfate (7758-98-7), (5.10) dichlofluanid (1085-98-9), (5.11) dithianon (3347-22-6), (5.12) dodine (2439-10-3), (5.13) dodine free base, (5.14) ferbam (14484-64-1), (5.15) fluorofolpet (719-96-0), (5.16) folpet (133-07-3), (5.17) guazatine (108173-90-6), (5.18) guazatine acetate, (5.19) iminoctadine (13516-27-3), (5.20) iminoctadine albesilate (169202-06-6), (5.21) iminoctadine triacetate (57520-17-9), (5.22) mancopper (53988-93-5), (5.23) mancozeb (8018-01-7), (5.24) maneb (12427-38-2), (5.25) metiram (9006-42-2), (5.26) metiram zinc (9006-42-2), (5.27) oxine-copper (10380-28-6), (5.28) propamidine (104-32-5), (5.29) propineb (12071-83-9), (5.30) sulphur and sulphur preparations including calcium polysulphide (7704-34-9), (5.31) thiram (137-26-8), (5.32) tolylfluanid (731-27-1), (5.33) zineb (12122-67-7), (5.34) ziram (137-30-4) and salts thereof.

(6) Compounds capable to induce a host defence, like for example (6.1) acibenzolar-5-methyl (135158-54-2), (6.2) isotianil (224049-04-1), (6.3) probenazole (27605-76-1), (6.4) tiadinil (223580-51-6) and salts thereof.

(7) Inhibitors of the amino acid and/or protein biosynthesis, for example, (7.1) andoprim (23951-85-1), (7.2) blasticidin-S (2079-00-7), (7.3) cyprodinil (121552-61-2), (7.4) kasugamycin (6980-18-3), (7.5) kasugamycin hydrochloride hydrate (19408-46-9), (7.6) mepanipyrim (110235-47-7), (7.7) pyrimethanil (53112-28-0) and salts thereof.

(8) Inhibitors of the ATP production, for example (8.1) fentin acetate (900-95-8), (8.2) fentin chloride (639-58-7), (8.3) fentin hydroxide (76-87-9) and (8.4) silthiofam (175217-20-6).

(9) Inhibitors of the cell wall synthesis, for example (9.1) benthiavalicarb (177406-68-7), (9.2) dimethomorph (110488-70-5), (9.3) flumorph (211867-47-9), (9.4) iprovalicarb (140923-17-7), (9.5) mandipropamid (374726-62-2), (9.6) polyoxins (11113-80-7), (9.7) polyoxorim (22976-86-9), (9.8) validamycin A (37248-47-8) and (9.9) valifenalate (283159-94-4; 283159-90-0).

(10) Inhibitors of the lipid and membrane synthesis, for example (10.1) biphenyl (92-52-4), (10.2) chloroneb (2675-77-6), (10.3) dicloran (99-30-9), (10.4) edifenphos (17109-49-8), (10.5) etridazole (2593-15-9), (10.6) iodocarb (55406-53-6), (10.7) iprobenfos (26087-47-8), (10.8) isoprothiolane (50512-35-1), (10.9) propamocarb (25606-41-1), (10.10) propamocarb hydrochloride (25606-41-1), (10.11) prothiocarb (19622-08-3), (10.12) pyrazophos (13457-18-6), (10.13) quintozene (82-68-8), (10.14) tecnazene (117-18-0) and (10.15) tolclofos-methyl (57018-04-9).

(11) Inhibitors of the melanine biosynthesis, for example (11.1) carpropamid (104030-54-8), (11.2) diclocymet (139920-32-4), (11.3) fenoxanil (115852-48-7), (11.4) phthalide (27355-22-2), (11.5) pyroquilon (57369-32-1) and (11.6) tricyclazole (41814-78-2).

(12) Inhibitors of the nucleic acid synthesis, for example (12.1) benalaxyl (71626-11-4), (12.2) benalaxyl-M (kiralaxyl) (98243-83-5), (12.3) bupirimate (41483-43-6), (12.4) clozylacon (67932-85-8), (12.5) dimethirimol (5221-53-4), (12.6) ethirimol (23947-60-6), (12.7) furalaxyl (57646-30-7), (12.8) hymexazol (10004-44-1), (12.9) metalaxyl (57837-19-1), (12.10) metalaxyl-M (mefenoxam) (70630-17-0), (12.11) ofurace (58810-48-3), (12.12) oxadixyl (77732-09-3) and (12.13) oxolinic acid (14698-29-4).

(13) Inhibitors of the signal transduction, for example (13.1) chlozolinate (84332-86-5), (13.2) fenpiclonil (74738-17-3), (13.3) fludioxonil (131341-86-1), (13.4) iprodione (36734-19-7), (13.5) procymidone (32809-16-8), (13.6) quinoxyfen (124495-18-7) and (13.7) vinclozolin (50471-44-8).

(14) Compounds capable to act as an uncoupler, like for example (14.1) binapacryl (485-31-4), (14.2) dinocap (131-72-6), (14.3) ferimzone (89269-64-7), (14.4) fluazinam (79622-59-6) and (14.5) meptyldinocap (131-72-6).

(15) Further compounds, like for example (15.1) benthiazole (21564-17-0), (15.2) bethoxazin (163269-30-5), (15.3) capsimycin (70694-08-5), (15.4) carvone (99-49-0), (15.5) chinomethionat (2439-01-2), (15.6) chlazafenone (688046-61-9), (15.7) cufraneb (11096-18-7), (15.8) cyflufenamid (180409-60-3), (15.9) cymoxanil (57966-95-7), (15.10) cyprosulfamide (221667-31-8), (15.11) dazomet (533-74-4), (15.12) debacarb (62732-91-6), (15.13) dichlorophen (97-23-4), (15.14) diclomezine (62865-36-5), (15.15) difenzoquat (49866-87-7), (15.16) difenzoquat methylsulphate (43222-48-6), (15.17) diphenylamine (122-39-4), (15.18) ecomate, (15.19) fenpyrazamine (473798-59-3), (15.20) flumetover (154025-04-4), (15.21) fluoroimide (41205-21-4), (15.22) flusulfamide (106917-52-6), (15.23) flutianil (304900-25-2), (15.24) fosetyl-aluminium (39148-24-8), (15.25) fosetyl-calcium, (15.26) fosetyl-sodium (39148-16-8), (15.27) hexachlorobenzene (118-74-1), (15.28) irumamycin (81604-73-1), (15.29) methasulfocarb (66952-49-6), (15.30) methyl isothiocyanate (556-61-6), (15.31) metrafenone (220899-03-6), (15.32) mildiomycin (67527-71-3), (15.33) natamycin (7681-93-8), (15.34) nickel dimethyldithiocarbamate (15521-65-0), (15.35) nitrothal-isopropyl (10552-74-6), (15.36) octhilinone (26530-20-1), (15.37) oxamocarb (917242-12-7), (15.38) oxyfenthiin (34407-87-9), (15.39) pentachlorophenol and salts (87-86-5), (15.40) phenothrin, (15.41) phosphorous acid and its salts (13598-36-2), (15.42) propamocarb-fosetylate, (15.43) propanosine-sodium (88498-02-6), (15.44) proquinazid (189278-12-4), (15.45) pyrrolnitrine (1018-71-9) (EP-A 1 559 320), (15.46) tebufloquin (376645-78-2), (15.47) tecloftalam (76280-91-6), (15.48) tolnifanide (304911-98-6), (15.49) triazoxide (72459-58-6), (15.50) trichlamide (70193-21-4), (15.51) zarilamid (84527-51-5), (15.52) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-79-6) (WO 2008013622), (15.53) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-80-9) (WO 2008013622), (15.54) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003318-67-9) (WO 2008013622), (15.55) 1-(4-methoxyphenoxy)-3,3-dimethylbutan-2-yl 1H-imidazole-1-carboxylate (111227-17-9), (15.56) 2,3,5,6-tetrachloro-4-(methylsulfonyl)pyridine (13108-52-6), (15.57) 2,3-dibutyl-6-chlorothieno[2,3-d]pyrimidin-4(3H)-one (221451-58-7), (15.58) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone (1003316-53-7) (WO 2008013622), (15.59) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone (1003316-54-8) (WO 2008013622), (15.60) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone (1003316-51-5) (WO 2008013622), (15.61) 2-butoxy-6-iodo-3-propyl-4H-chromen-4-one, (15.62) 2-chloro-5-[2-chloro-1-(2,6-difluoro-4-methoxyphenyl)-4-methyl-1H-imidazol-5-yl]pyridine, (15.63) 2-phenylphenol and salts (90-43-7), (15.64) 3,4,5-trichloropyridine-2,6-dicarbonitrile (17824-85-0), (15.65) 3-[5-(4-chlorophenyl)-2,3-dimethyl-1,2-oxazolidin-3-yl]pyridine, (15.66) 3-chloro-5-(4-chlorophenyl)-4-(2,6-difluorophenyl)-6-methylpyridazine, (15.67) 4-(4-chlorophenyl)-5-(2,6-difluorophenyl)-3,6-dimethylpyridazine, (15.68) 5-amino-1,3,4-thiadiazole-2-thiol, (15.69) 5-chloro-N'-phenyl-N'-(prop-2-yn-1-yl)thiophene-2-sulfonohydrazide (134-31-6), (15.70) 5-methyl-6-octyl[1,2,4]triazolo[1,5-a]pyrimidin-7-amine, (15.71) ethyl (2Z)-3-amino-2-cyano-3-phenylprop-2-enoate, (15.72) N-(4-chlorobenzyl)-3-[3-methoxy-4-(prop-2-yn-1-yloxy)phenyl]propanamide, (15.73) N-[(4-chlorophenyl)(cyano)methyl]-3-[3-methoxy-4-(prop-2-yn-1-yloxy)phenyl]propanamide, (15.74) N-[(5-bromo-3-chloropyridin-2-yl)methyl]-2,4-dichloropyridine-3-carboxamide, (15.75) N-[1-(5-bromo-3-chloropyridin-2-yl)ethyl]-2,4-dichloropyridine-3-carboxamide, (15.76) N-[1-(5-bromo-3-chloropyridin-2-yl)ethyl]-2-fluoro-4-iodopyridine-3-carboxamide, (15.77) N-{(E)-[(cyclopropylmethoxy)imino][6-(difluoromethoxy)-2,3-difluorophenyl]methyl}-2-phenylacetamide (221201-92-9), (15.78) N-{(Z)-[(cyclopropylmethoxy)imino][6-(difluoromethoxy)-2,3-difluorophenyl]methyl}-2-phenylacetamide (221201-92-9), (15.79) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide (922514-49-6) (WO 2007014290), (15.80) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide (922514-07-6) (WO 2007014290), (15.81) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide (922514-48-5) (WO 2007014290), (15.82) pentyl {6-[({[(1-methyl-1H-tetrazol-5-yl)(phenyl)methylidene]amino}oxy)methyl]pyridin-2-yl}carbamate, (15.83) phenazine-1-carboxylic acid, (15.84) quinolin-8-ol (134-31-6) and (15.85) quinolin-8-ol sulfate (2:1) (134-31-6).

(16) Further compounds, like for example (2.28) 1-methyl-3-(trifluoromethyl)-N-[2'-(trifluoromethyl)biphenyl-2-yl]-1H-pyrazole-4-carboxamide, (2.29) N-(4'-chlorobiphenyl-2-yl)-3-(difluoromethyl)-1-methyl-1H-pyrazole-4-carboxamide, (2.30) N-(2',4'-dichlorobiphenyl-2-yl)-3-(difluoromethyl)-1-methyl-1H-pyrazole-4-carboxamide, (2.31) 3-(difluoromethyl)-1-methyl-N-[4'-(trifluoromethyl)biphenyl-2-yl]-1H-pyrazole-4-carboxamide, (2.32) N-(2',5'-difluorobiphenyl-2-yl)-1-methyl-3-(trifluoromethyl)-1H-pyrazole-4-carboxamide, (2.33) 3-(difluoromethyl)-1-methyl-N-[4'-(prop-1-yn-1-yl)biphenyl-2-yl]-1H-pyrazole-4-carboxamide (known from WO 2004/058723), (2.34) 5-fluoro-1,3-dimethyl-N-[4'-(prop-1-yn-1-yl)biphenyl-2-yl]-1H-pyrazole-4-carboxamide (known from WO 2004/058723), (2.35) 2-chloro-N-[4'-(prop-1-yn-1-yl)biphenyl-2-yl]pyridine-3-carboxamide (known from WO 2004/058723), (2.36) 3-(difluoromethyl)-N-[4'-(3,3-dimethylbut-1-yn-1-yl)

biphenyl-2-yl]-1-methyl-1H-pyrazole-4-carboxamide (known from WO 2004/058723), (2.37) N-[4'-(3,3-dimethylbut-1-yn-1-yl)biphenyl-2-yl]-5-fluoro-1,3-dimethyl-1H-pyrazole-4-carboxamide (known from WO 2004/058723), (2.38) 3-(difluoromethyl)-N-(4'-ethynylbiphenyl-2-yl)-1-methyl-1H-pyrazole-4-carboxamide (known from WO 2004/058723), (2.39) N-(4'-ethynylbiphenyl-2-yl)-5-fluoro-1,3-dimethyl-1H-pyrazole-4-carboxamide (known from WO 2004/058723), (2.40) 2-chloro-N-(4'-ethynylbiphenyl-2-yl)pyridine-3-carboxamide (known from WO 2004/058723), (2.41) 2-chloro-N-[4'-(3,3-dimethylbut-1-yn-1-yl)biphenyl-2-yl]pyridine-3-carboxamide (known from WO 2004/058723), (2.42) 4-(difluoromethyl)-2-methyl-N-[4'-(trifluoromethyl)biphenyl-2-yl]-1,3-thiazole-5-carboxamide (known from WO 2004/058723), (2.43) 5-fluoro-N-[4'-(3-hydroxy-3-methylbut-1-yn-1-yl)biphenyl-2-yl]-1,3-dimethyl-1H-pyrazole-4-carboxamide (known from WO 2004/058723), (2.44) 2-chloro-N-[4'-(3-hydroxy-3-methylbut-1-yn-1-yl)biphenyl-2-yl]pyridine-3-carboxamide (known from WO 2004/058723), (2.45) 3-(difluoromethyl)-N-[4'-(3-methoxy-3-methylbut-1-yn-1-yl)biphenyl-2-yl]-1-methyl-1H-pyrazole-4-carboxamide (known from WO 2004/058723), (2.46) 5-fluoro-N-[4'-(3-methoxy-3-methylbut-1-yn-1-yl)biphenyl-2-yl]-1,3-dimethyl-1H-pyrazole-4-carboxamide (known from WO 2004/058723), (2.47) 2-chloro-N-[4'-(3-methoxy-3-methylbut-1-yn-1-yl)biphenyl-2-yl]pyridine-3-carboxamide (known from WO 2004/058723) and salts thereof, (15.86) (5-bromo-2-methoxy-4-methylpyridin-3-yl)(2,3,4-trimethoxy-6-methylphenyl)methanone (known from EP-A 1 559 320) and (9.10) N-[2-(4-{[3-(4-chlorophenyl)prop-2-yn-1-yl]oxy}-3-methoxyphenyl)ethyl]-N2-(methylsulfonyl)valinamide (220706-93-4).

Examples of suitable insecticide, acaricide or nematicide mixing partners may be selected in the following lists, wherein the active ingredients specified in this description by their "common name" are known, for example, from "The Pesticide Manual", 14th Ed., British Crop Protection Council 2006, and from the Web page http://www.alanwood.net/pesticides.

(1) Acetylcholinesterase (AChE) inhibitors, for example
carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC, and xylylcarb; or
organophosphates, e.g. acephate, azamethiphos, azinphos (-methyl, -ethyl), cadusafos, chlorethoxyfos, chlorfenvinphos, chlorfenvinphos, chlormephos, chlorpyrifos (-methyl), coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion (-methyl), phenthoate, phorate, phosalone, phosmet, phosphamidon, phoxim, pirimiphos (-methyl), profenofos, propetamphos, prothiofos, pyraclofos, pyridaphenthion, quinalphos, sulfotep, tebupirimfos, temephos, terbufos, tetrachlorvinphos, thiometon, triazophos, triclorfon, and vamidothion.

(2) GABA-gated chloride channel antagonists, for example
organochlorines, e.g. chlordane, endosulfan (alpha-); or
fiproles (phenylpyrazoles), e.g. ethiprole, fipronil, pyrafluprole, and pyriprole.

(3) Sodium channel modulators/voltage-dependent sodium channel blockers, for example
pyrethroids, e.g. acrinathrin, allethrin (d-cis-trans, d-trans), bifenthrin, bioallethrin, bioallethrin S-cyclopentenyl, bioresmethrin, cycloprothrin, cyfluthrin (beta-), cyhalothrin (gamma-, lambda-), cypermethrin (alpha-, beta-, theta-, zeta-), cyphenothrin [(1R)-trans-isomers], deltamethrin, dimefluthrin, empenthrin [(EZ)-(1R)-isomers), esfenvalerate, etofenprox, fenpropathrin, fenvalerate, flucythrinate, flumethrin, fluvalinate (tau-), halfenprox, imiprothrin, metofluthrin, permethrin, phenothrin [(1R)-trans-isomer), prallethrin, profluthrin, pyrethrin (pyrethrum), resmethrin, RU 15525, silafluofen, tefluthrin, tetramethrin [(1R)-isomers)], tralomethrin, transfluthrin and ZXI 8901; or
DDT; or methoxychlor.

(4) Nicotinergic acetylcholine receptor agonists, for example
chloronicotinyls, e.g. acetamiprid, clothianidin, dinotefuran, imidacloprid, nitenpyram, thiacloprid, thiamethoxam; or
nicotine.

(5) Allosteric acetylcholine receptor modulators (agonists), for example
spinosyns, e.g. spinetoram and spinosad.

(6) Chloride channel activators, for example
avermectins/milbemycins, e.g. abamectin, emamectin benzoate, lepimectin, and milbemectin.

(7) Juvenile hormone mimics, e.g. hydroprene, kinoprene, methoprene; or fenoxycarb; pyriproxyfen.

(8) Miscellaneous non-specific (multi-site) inhibitors, for example
gassing agents, e.g. methyl bromide and other alkyl halides; or chloropicrin; sulfuryl fluoride; borax; tartar emetic.

(9) Selective homopteran feeding blockers, e.g. pymetrozine; or flonicamid.

(10) Mite growth inhibitors, e.g. clofentezine, diflovidazin, hexythiazox, etoxazole.

(11) Microbial disruptors of insect midgut membranes, e.g. Bacillus thuringiensis subspecies israelensis, Bacillus sphaericus, Bacillus thuringiensis subspecies aizawai, Bacillus thuringiensis subspecies kurstaki, Bacillus thuringiensis subspecies tenebrionis, and BT crop proteins: Cry1Ab, Cry1Ac, Cry1Fa, Cry2Ab, mCry3A, Cry3Ab, Cry3Bb, Cry34/35Ab1.

(12) Inhibitors of mitochondrial ATP synthase, for example diafenthiuron; or
organotin miticides, e.g. azocyclotin, cyhexatin, and fenbutatin oxide; or
propargite; tetradifon.

(13) Uncouplers of oxidative phoshorylation via disruption of the proton gradient, for example chlorfenapyr, and DNOC.

(14) Nicotinic acetylcholine receptor channel blockers, for example bensultap, cartap hydrochloride, thiocyclam, and thiosultap-sodium.

(15) Inhibitors of chitin biosynthesis, type 0, for example benzoylureas, e.g. bistrifluoron, chlorfluazuron, diflubenzuron, flucycloxuron, flufenoxuron, hexaflumuron, lufenuron, novaluron, noviflumuron, penfluoron, teflubenzuron, and triflumuron.

(16) Inhibitors of chitin biosynthesis, type 1, for example buprofezin.

(17) Moulting disruptors, for example cyromazine.

(18) Ecdysone receptor agonists/disruptors, for example diacylhydrazines, e.g. chromafenozide, halofenozide, methoxyfenozide, and tebufenozide.

(19) Octopamine receptor agonists, for example amitraz.

(20) Mitochondrial complex III electron transport inhibitors (Coupling site II), for example hydramethylnon; acequinocyl; fluacrypyrim; or cyflumetofen and cyenopyrafen.

(21) Mitochondrial complex I electron transport inhibitors, for example
METI acaricides, e.g. fenazaquin, fenpyroximate, pyrimidifen, pyridaben, tebufenpyrad, tolfenpyrad;
or rotenone. (Derris).
(22) Voltage-dependent sodium channel blockers, e.g. indoxacarb; metaflumizone.
(23) Inhibitors of acetyl CoA carboxylase, for example tetronic acid derivatives, e.g. spirodiclofen and spiromesifen; or
tetramic acid derivatives, e.g. spirotetramat.
(24) Mitochondrial complex IV electron inhibitors, for example phosphines, e.g. aluminium phosphide, calcium phosphide, phosphine, and zinc phosphide;
or cyanide.
(28) Ryanodine receptor modulators, for example diamides, e.g. chlorantraniliprole (Rynaxypyr), Cyantraniliprole (Cyazypyr), and flubendiamide.

Further active ingredients with unknown or uncertain mode of action, for example azadirachtin, amidoflumet, benzoximate, bifenazate, chinomethionat, cryolite, dicofol, flufenerim, pyridalyl, and pyrifluquinazon; or one of the following known active compounds
4-{[(6-brompyrid-3-yl)methyl](2-fluorethyl)amino}furan-2(5H)-on (known from WO 2007/115644), 4-{[(6-fluorpyrid-3-yl)methyl](2,2-difluorethyl)amino}furan-2(5H)-on
(known from WO 2007/115644), 4-{[(2-chlor-1,3-thiazol-5-yl)methyl](2-fluorethyl)amino}furan-2(5H)-on (known from WO 2007/115644), 4-{[(6-chlorpyrid-3-yl)methyl](2-fluorethyl)amino}furan-2(5H)-on (known from WO 2007/115644), 4-{[(6-chlorpyrid-3-yl)methyl](2,2-difluorethyl)amino}furan-2(5H)-on known from WO 2007/115644), 4-{[(6-chlor-5-fluorpyrid-3-yl)methyl](methyl)amino}furan-2(5H)-on (known from WO 2007/115643), 4-{[(5,6-dichlorpyrid-3-yl)methyl](2-fluorethyl)amino}furan-2(5H)-on (known from WO 2007/115646), 4-{[(6-chlor-5-fluorpyrid-3-yl)methyl](cyclopropyl)amino}furan-2(5H)-on (known from WO 2007/115643), 4-{[(6-chlorpyrid-3-yl)methyl](cyclopropyl)amino}furan-2(5H)-on (known from EP-A-0 539 588), 4-{[(6-chlorpyrid-3-yl)methyl](methyl)amino}furan-2(5H)-on (known from EP-A-0 539 588), [(6-chlorpyridin-3-yl)methyl](methyl)oxido-$\lambda^4$-sulfanylidencyanamid (known from WO 2007/149134), [1-(6-chlorpyridin-3-yl)ethyl](methypoxido-$\lambda^4$-sulfanylidencyanamid (known from WO 2007/149134) and its diastereomeres (A) and (B)

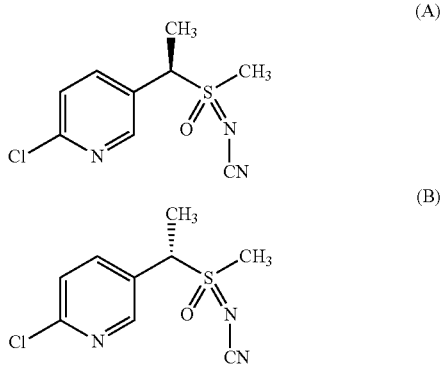

(also known from WO 2007/149134), [(6-trifluormethylpyridin-3-yl)methyl](methyl)oxido-$\lambda^4$-sulfanylidencyanamid (known from WO 2007/095229), or sulfoxaflor (also known from WO 2007/149134),
11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5]dec-3-en-2-one (known from WO 2008/067911), and 1-{2,4-dimethyl-5-[(2,2,2-trifluoroethyl)sulfinyl]phenyl}-3-(trifluoromethyl)-1H-1,2,4-triazole (known from WO 1999/55668).

In an other embodiment of the invention, the composition further comprises plant growth regulators and plant activators.

Examples of plant growth regulators include, but are not limited to antiauxins (clofibric acid, 2,3,5-tri-iodobenzoic acid), auxins (4-CPA, 2,4-D, 2,4-DB, 2,4-DEP, dichlorprop, fenoprop, IAA, IBA, naphthaleneacetamide, [alpha]-naphthaleneacetic acid, 1-naphthol, naphthoxyacetic acid, potassium naphthenate, sodium naphthenate, 2,4,5-T), cytokinins (2iP, benzyladenine, kinetin, zeatin), defoliants (calcium cyanamide, dimethipin, endothal, ethephon, merphos, metoxuron, pentachlorophenol, thidiazuron, tribufos), ethylene inhibitors (aviglycine, 1-methylcyclopropene), ethylene releasers (ACC, etacelasil, ethephon, glyoxime), gibberellins (gibberellic acid, gibberellins, including non-cyclopropene compounds that show gibberellin-like activity, such as, for example, helminthosporic acid, phaseolic acid, kaurenoic acid, and steviol), growth inhibitors (abscisic acid, ancymidol, butralin, carbaryl, chlorphonium, chlorpropham, dikegulac, flumetralin, fluoridamid, fosamine, glyphosine, isopyrimol, jasmonic acid, maleic hydrazide, mepiquat, piproctanyl, prohydrojasmon, propham, 2,3,5-tri-iodobenzoic acid), morphactins (chlorfluren, chlorflurenol, dichlorflurenol, flurenol), growth retardants/modifiers (chlormequat, daminozide, flurprimidol, mefluidide, paclobutrazol, cyproconazole, tetcyclacis, uniconazole, ancymidol, trinexapac-ethyl, and progexadione-CA), growth stimulators (brassinolide, forchlorfenuron, hymexazol, 2-amino-6-oxypurine derivatives, as described below, indolinone derivates, as described below, 3,4-disubstituted maleimide derivatives, as described below, and fused azepinone derivatives, as described below). The term additionally includes other active ingredients such as benzofluor, buminafos, carvone, ciobutide, clofencet, cloxyfonac, cyclanilide, cycloheximide, epocholeone, ethychlozate, ethylene, fenridazon, heptopargil, holosulf, inabenfide, karetazan, lead arsenate, methasulfocarb, prohexadione, pydanon, sintofen, triapenthenol, and trinexapac. Additional plant growth regulators include indolinone derivative plant stimulators described in WO 2005/107466; 3,4-disubstituted maleimide derivatives described in WO 2005/107465; fused azepinone derivatives described in WO 2005/107471; and 2-amino-6-oxypurine derivatives described in WO 2005/107472.

Active ingredients concentration in the composition generally corresponds directly or after dilution to the use rate for this particular active ingredient. The use rate for strigolactone compounds is generally from 1 µg to 1 g/ha; the use rate for LCO compounds is generally from 1 µg to 100 g/ha; the use rate for pesticidal active ingredient is generally from 1 g to 1000 g/ha.

A man of ordinary skill in the art would be able to determine the adequate ratios according to the methods of application and to the compounds.

The composition according to the present invention may further comprise another additional component such as an agriculturally acceptable support, carrier or filler.

In the present specification, the term "support" denotes a natural or synthetic, organic or inorganic material with which the active material is combined to make it easier to apply, notably to the parts of the plant. This support is thus generally inert and should be agriculturally acceptable. The support may be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports may also be used.

The composition may also comprise other additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active material and/or the inert support are water-insoluble and when the vector agent for the application is water. Preferably, surfactant content may be comprised between 5% and 40% by weight of the composition.

Additional components may also be included, e.g. protective colloids, adhesives, thickeners, thixotropic agents, penetration agents, stabilisers, sequestering agents. More generally, the active materials can be combined with any solid or liquid additive, which complies with the usual formulation techniques.

In general, the composition according to the invention may contain from 0.00000005 to 99% (by weight) of active material, preferably 0.0000001 to 70% by weight.

Compositions according to the present invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ulv) liquid, ultra low volume (ulv) suspension, water dispersible granules or tablets, water dispersible powder for slurry treatment, water soluble granules or tablets, water soluble powder for seed treatment and wettable powder.

These compositions include not only compositions which are ready to be applied to the plant or seed to be treated, or in furrow in the soil, by means of a suitable device, such as a spraying or dusting device, but also concentrated commercial compositions which must be diluted before they are applied to the crop.

The compositions of the present invention may be used to to increase the yield, growth, or vigor of the plant, and/or for curatively or preventively control pests of crops, as phytopathogenic fungi, insects, nematodes, acarid.

Thus, according to a further aspect, the present invention provides a method for curatively or preventively controlling pests of crops, as phytopathogenic fungi, insects, nematodes, acarid, and/or increasing the yield, growth or vigor of a plant characterised in that a composition according to the invention is applied via seed treatment, foliar application, stem application, drench/drip application (chemigation) to the seed, the plant or to the fruit of the plant, or to soil, particularly in furrow, and/or to inert substrate (e.g. inorganic substrates (e.g. sand, rockwool, glasswool, expanded minerals (e.g. perlite, vermiculite, zeolite, expanded clay)), Pumice, Pyroclastic materials/tuff, synthetic organic substrates (e.g. Polyurethane), organic substrates (e.g. peat, composts, tree waste products (e.g. coir, wood fibre/chips, tree bark)) and/or to a liquid substrate (e.g. floating hydroponic systems, Nutrient Film Technique, Aeroponics) wherein the plant is growing or wherein it is desired to grow.

The composition as used against pests and diseases of crops comprises an effective and non-phytotoxic amount of a pesticidal compound.

The expression "effective and non-phytotoxic amount" means an amount of composition according to the invention which is sufficient to control or destroy the pests and diseases present or liable to appear on the crops, and which does not entail any appreciable symptom of phytotoxicity for the said crops. Such an amount can vary within a wide range depending on the pests and diseases to be combated or controlled, the type of crop, the climatic conditions and the compounds included in the composition according to the invention.

This amount can be determined by systematic field trials, which are within the capabilities of a person skilled in the art.

The method of treatment according to the present invention is useful to treat propagation material such as tubers or rhizomes, but also seeds, seedlings or seedlings pricking out and plants or plants pricking out. This method of treatment can also be useful to treat roots. The method of treatment according to the present invention can also be useful to treat the overground parts of the plant such as trunks, stems or stalks, leaves, flowers and fruit of the concerned plant.

Among the plants that can be treated by the method according to the present invention, mention may be made of cotton; flax; vine; fruit or vegetable crops such as *Rosaceae* sp. (for instance pip fruit such as apples and pears, but also stone fruit such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., Actimidaceae sp., *Lauraceae* sp., *Musaceae* sp. (for instance banana trees and plantins), *Rubiaceae* sp., *Theaceae* sp., *Sterculiceae* sp., *Rutaceae* sp. (for instance lemons, oranges and grapefruit); *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); major crops such as *Graminae* sp. (for instance maize, lawn or cereals such as wheat, rice, barley and triticale), *Asteraceae* sp. (for instance sunflower), *Cruciferae* sp. (for instance oil seed rape), *Fabacae* sp. (for instance peanuts), *Papilionaceae* sp. (for instance soybean), *Solanaceae* sp. (for instance potatoes), *Chenopodiaceae* sp. (for instance beetroots); horticultural and forest crops; as well as genetically modified homologues of these crops.

Among the diseases of plants or crops that can be controlled by the method according to the present invention, mention may be made of:

Powdery Mildew Diseases such as

*Blumeria* diseases caused for example by *Blumeria graminis;*

*Podosphaera* diseases caused for example by *Podosphaera leucotricha;*

*Sphaerotheca* diseases caused for example by *Sphaerotheca fuliginea;*

*Uncinula* diseases caused for example by *Uncinula necator;*

Rust Diseases such as

*Gymnosporangium* diseases caused for example by *Gymnosporangium sabinae;*

*Hemileia* diseases caused for example by *Hemileia vastatrix*;
*Phakopsora* diseases caused for example by *Phakopsora pachyrhizi* and *Phakopsora meibomiae*;
*Puccinia* diseases caused for example by *Puccinia recondite*, *Puccinia graminis* or *Puccinia striiformis*;
*Uromyces* diseases caused for example by *Uromyces appendiculatus*;

Oomycete Diseases such as
*Albugo* diseases caused for example by *Albugo candida*;
*Bremia* diseases caused for example by *Bremia lactucae*;
*Peronospora* diseases caused for example by *Peronospora pisi* and *Peronospora brassicae*;
*Phytophthora* diseases caused for example by *Phytophthora infestans*;
*Plasmopara* diseases caused for example by *Plasmopara viticola*;
*Pseudoperonospora* diseases caused for example by *Pseudoperonospora humuli* and *Pseudoperonospora cubensis*;
*Pythium* diseases caused for example by *Pythium ultimum*;

Leaf spot, Leaf blotch and Leaf Blight Diseases such as
*Alternaria* diseases caused for example by *Alternaria solani*;
*Cercospora* diseases caused for example by *Cercospora beticola*;
*Cladiosporium* diseases caused for example by *Cladiosporium cucumerinum*;
*Cochliobolus* diseases caused for example by *Cochliobolus sativus* (*Conidiaform*: *Drechslera*, Syn: *Helminthosporium*) or *Cochliobolus miyabeanus*;
*Colletotrichum* diseases caused for example by *Colletotrichum lindemuthianum*;
*Cycloconium* diseases caused for example by *Cycloconium oleaginum*;
*Diaporthe* diseases caused for example by *Diaporthe citri*;
*Elsinoe* diseases caused for example by *Elsinoe fawcettii*;
*Gloeosporium* diseases caused for example by *Gloeosporium laeticolor*;
*Glomerella* diseases caused for example by *Glomerella cingulata*;
*Guignardia* diseases caused for example by *Guignardia bidwellii*;
*Leptosphaeria* diseases caused for example by *Leptosphaeria maculans* and *Leptosphaeria nodorum*;
*Magnaporthe* diseases caused for example by *Magnaporthe grisea*;
*Mycosphaerella* diseases caused for example by *Mycosphaerella graminicola*, *Mycosphaerella arachidicola* and *Mycosphaerella fijiensis*;
*Phaeosphaeria* diseases caused for example by *Phaeosphaeria nodorum*;
*Pyrenophora* diseases caused for example by *Pyrenophora teres* or *Pyrenophora tritici repentis*;
*Ramularia*-diseases caused for example by *Ramularia collocygni* or *Ramularia areola*;
*Rhynchosporium* diseases caused for example by *Rhynchosporium secalis*;
*Septoria* diseases caused for example by *Septoria apii* and *Septoria lycopersici*;
*Typhula* diseases caused for example by *Thyphula incarnate*;
*Venturia* diseases caused for example by *Venturia inaequalis*;

Root-, Sheath and Stem Diseases such as
*Corticium* diseases caused for example by *Corticium graminearum*;
*Fusarium* diseases caused for example by *Fusarium oxysporum*;
*Gaeumannomyces* diseases caused for example by *Gaeumannomyces graminis*;
*Rhizoctonia* diseases caused for example by *Rhizoctonia solani*;
*Sarocladium* diseases caused for example by *Sarocladium oryzae*;
*Sclerotium* diseases caused for example by *Sclerotium oryzae*;
*Tapesia* diseases caused for example by *Tapesia acuformis*;
*Thielaviopsis* diseases caused for example by *Thielaviopsis basicola*;

Ear and Panicle Diseases including Maize cob such as
*Alternaria* diseases caused for example by *Alternaria* spp.;
*Aspergillus* diseases caused for example by *Aspergillus flavus*;
*Cladosporium* diseases caused for example by *Cladosporium cladosporioides*;
*Claviceps* diseases caused for example by *Claviceps purpurea*;
*Fusarium* diseases caused for example by *Fusarium culmorum*;
*Gibberella* diseases caused for example by *Gibberella zeae*;
*Monographella* diseases caused for example by *Monographella nivalis*;

Smut- and Bunt Diseases such as
*Sphacelotheca* diseases caused for example by *Sphacelotheca reiliana*;
*Tilletia* diseases caused for example by *Tilletia caries*;
*Urocystis* diseases caused for example by *Urocystis occulta*;
*Ustilago* diseases caused for example by *Ustilago nuda*;

Fruit Rot and Mould Diseases such as
*Aspergillus* diseases caused for example by *Aspergillus flavus*;
*Botrytis* diseases caused for example by *Botrytis cinerea*;
*Penicillium* diseases caused for example by *Penicillium expansum* and *Penicillium purpurogenum*;
*Rhizopus* diseases caused by example by *Rhizopus stolonifer*
*Sclerotinia* diseases caused for example by *Sclerotinia sclerotiorum*;
*Verticillium* diseases caused for example by *Verticillium alboatrum*;

Seed- and Soilborne Decay, Mould, Wilt, Rot and Damping-off diseases
*Alternaria* diseases caused for example by *Alternaria brassicicola*;
*Aphanomyces* diseases caused for example by *Aphanomyces euteiches*;
*Ascochyta* diseases caused for example by *Ascochyta lentis*;
*Aspergillus* diseases caused for example by *Aspergillus flavus*;
*Cladosporium* diseases caused for example by *Cladosporium herbarum*;
*Cochliobolus* diseases caused for example by *Cochliobolus sativus*;
(*Conidiaform*: *Drechslera*, *Bipolaris* Syn: *Helminthosporium*);
*Colletotrichum* diseases caused for example by *Colletotrichum coccodes*;
*Fusarium* diseases caused for example by *Fusarium culmorum*;
*Gibberella* diseases caused for example by *Gibberella zeae*;
*Macrophomina* diseases caused for example by *Macrophomina phaseolina*;
*Microdochium* diseases caused for example by *Microdochium nivale*;
*Monographella* diseases caused for example by *Monographella nivalis*;
*Penicillium* diseases caused for example by *Penicillium expansum*;

*Phoma* diseases caused for example by *Phoma lingam;*
*Phomopsis* diseases caused for example by *Phomopsis sojae;*
*Phytophthora* diseases caused for example by *Phytophthora cactorum;*
*Pyrenophora* diseases caused for example by *Pyrenophora graminea;*
*Pyricularia* diseases caused for example by *Pyricularia oryzae;*
*Pythium* diseases caused for example by *Pythium ultimum;*
*Rhizoctonia* diseases caused for example by *Rhizoctonia solani;*
*Rhizopus* diseases caused for example by *Rhizopus oryzae;*
*Sclerotium* diseases caused for example by *Sclerotium rolfsii;*
*Septoria* diseases caused for example by *Septoria nodorum;*
*Typhula* diseases caused for example by *Typhula incarnate;*
*Verticillium* diseases caused for example by *Verticillium dahliae;*

Canker, Broom and Dieback Diseases such as
*Nectria* diseases caused for example by *Nectria galligena;*

Blight Diseases such as
*Monilinia* diseases caused for example by *Monilinia laxa;*

Leaf Blister or Leaf Curl Diseases including deformation of blooms and fruits such as
*Exobasidium* diseases caused for example by *Exobasidium vexans.*
*Taphrina* diseases caused for example by *Taphrina deformans;*

Decline Diseases of Wooden Plants such as
*Esca* disease caused for example by *Phaeomoniella clamydospora, Phaeoacremonium aleophilum* and *Fomitiporia mediterranea;*
*Ganoderma* diseases caused for example by *Ganoderma boninense;*
*Rigidoporus* diseases caused for example by *Rigidoporus lignosus*

Diseases of Flowers and Seeds such as
*Botrytis* diseases caused for example by *Botrytis cinerea;*

Diseases of Tubers such as
*Rhizoctonia* diseases caused for example by *Rhizoctonia solani;*
*Helminthosporium* diseases caused for example by *Helminthosporium solani;*

Club root diseases such as
*Plasmodiophora* diseases, cause for example by *Plamodiophora brassicae.*

Diseases caused by Bacterial Organisms such as
*Xanthomonas* species for example *Xanthomonas campestris* pv. *oryzae;*
*Pseudomonas* species for example *Pseudomonas syringae* pv. *lachrymans;*
*Erwinia* species for example *Erwinia amylovora.*

The composition according to the present invention is well tolerated by plants, have favourable homeotherm toxicity and are environmentally friendly; it is suitable for protecting plants and plant organs, for increasing harvest yields, for improving the quality of the harvested material and for controlling animal pests, in particular insects, arachnids and nematodes encountered in agriculture, in forests, in gardens and leisure facilities, in the protection of stored products and materials and in the hygiene sector. It is preferably used as crop protection agents. It is active against normally sensitive and resistant species and against all or some stages of development. Among the animal pests that can also be controlled by the method according to the present invention, mention may be made of:

Pest from the order of the Isopoda, for example, *Oniscus asellus, Armadillidium vulgare* and *Porcellio scaber;*

Pest from the order of the Diplopoda, for example, *Blaniulus guttulatus;*

Pest from the order of the Chilopoda, for example, *Geophilus carpophagus* and *Scutigera* spp.;

Pest from the order of the Symphyla, for example, *Scutigerella immaculate;*

Pest from the order of the Thysanura, for example, *Lepisma saccharine.*

Pest from the order of the Collembola, for example, *Onychiurus armatus;*

Pest from the order of the Orthoptera, for example, *Acheta domesticus, Gryllotalpa* spp., *Locusta migratoria migratorioides, Melanoplus* spp. and *Schistocerca gregaria;*

Pest from the order of the Blattaria, for example, *Blatta orientalis, Periplaneta americana, Leucophaea maderae* and *Blattella germanica;*

Pest from the order of the Dermaptera, for example, *Forficula auricularia;*

Pest from the order of the Isoptera, for example, *Reticulitermes* spp.;

Pest from the order of the Phthiraptera, for example, *Pediculus humanus corporis, Haematopinus* spp., *Linognathus* spp., *Trichodectes* spp., *Damalinia* spp.;

Pest from the order of the Thysanoptera, for example, *Hercinothrips femoralis, Thrips tabaci, Thrips palmi, Frankliniella accidentalis;*

Pest from the order of the Heteroptera, for example, *Eurygaster* spp., *Dysdercus intermedius, Piesma quadrate, Cimex lectularius, Rhodnius prolixus* and *Triatoma* spp.;

Pest from the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.;

Pest from the order of the Lepidoptera, for example, *Pectinophora gossypiella, Bupalus piniarius, Chematobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia am biguella, Homona magnanima, Tortrix viridana, Cnaphalocerus* spp. *and Oulema oryzae;*

Pest from the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gib-*

*bium psylloides, Tribolium* spp., *Tenebrio molitor, Agriotes* spp., *Conoderus* spp., *Melolontha melolontha, Amphimallon solstitialis, Costelytra zealandica* and *Lissorhoptrus oryzophilus;*

Pest from the order of the Hymenoptera, for example, *Diprion* spp., *Hoplocampa* spp., *Lasius* spp., *Monomorium pharaonis* and *Vespa* spp.;

Pest from the order of the Diptera, for *example, Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. *and Liriomyza* spp.;

Pest from the order of the Siphonaptera, for example, *Xenopsylla cheopis* and *Ceratophyllus* spp.; Pest from the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp. *and Brevipalpus* spp.;

The plant-parasitic nematodes such as Pratylenchus spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp. and *Bursaphelenchus* spp.

The pesticidal composition according to the present invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds of the present invention, or a composition according to the invention; this includes for example direct application, spraying, dipping, injection or any other suitable means.

LCO compounds, strigolactones compounds, combinations comprising LCO compounds and strigolactones compounds, eventually in combination with fungicides, insecticides, or other additives, can be used in the treatment of genetically modified organisms (GMOs), e.g. plants or seeds.

Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology or RNA interference—RNAi-technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted microorganisms. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted microorganisms, the treated plants display a substantial degree of resistance to these microorganisms. In the present case, unwanted microorganisms are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 21 days, preferably 1 to 14 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Examples of plants with the above-mentioned traits are non-exhaustively listed in Table A.

Plants that may be treated according to the invention are hybrid plants that already express the characteristic of heterosis or hybrid vigor which results in generally higher yield, vigor, health and resistance towards biotic and abiotic stresses). Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species (WO 92/05251, WO 95/09910, WO 98/27806, WO 05/002324, WO 06/021972 and U.S. Pat. No. 6,229,072). However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar (e.g. WO 91/02069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-resistant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science 221, 370-371), the CP4 gene of the bacterium *Agrobacterium* sp. (Barry et al., 1992, Curr. Topics Plant Physiol. 7, 139-145), the genes encoding a Petunia EPSPS (Shah et al., 1986, Science 233, 478-481), a Tomato EPSPS (Gasser et al., 1988, J. Biol. Chem. 263, 4280-4289), or an *Eleusine* EPSPS (WO 01/66704). It can also be a mutated EPSPS as described in for example EP 0837944, WO 00/66746, WO 00/66747 or WO02/26995. Glyphosate-tolerant plants can also be obtained by expressing a gene that encodes a glyphosate oxido-reductase enzyme as described in U.S. Pat. Nos. 5,776,760 and 5,463,175. Glyphosate-tolerant plants can also be obtained by expressing a gene that encodes a glyphosate acetyl transferase enzyme as described in for example WO 02/36782, WO 03/092360, WO 05/012515 and WO 07/024,782. Glyphosate-tolerant plants can also be obtained by selecting plants containing naturally-occurring mutations of the above-mentioned genes, as described in for example WO 01/024615 or WO 03/013226.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. Nos. 5,561,236; 5,648,477; 5,646,024; 5,273,894; 5,637,489; 5,276,268; 5,739,082; 5,908,810 and 7,112,665.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated HPPD enzyme as described in WO 96/38567, WO 99/24585 and WO 99/24586. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme prephenate deshydrogenase in addition to a gene encoding an HPPD-tolerant enzyme, as described in WO 2004/024928.

Still further herbicide resistant plants are plants that are made tolerant to acetolactate synthase (ALS) inhibitors. Known ALS-inhibitors include, for example, sulfonylurea, imidazolinone, triazolopyrimidines, pryimidinyoxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright (2002, Weed Science 50:700-712), but also, in U.S. Pat. Nos. 5,605,011, 5,378,824, 5,141,870, and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270. Other imidazolinone-tolerant plants are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerant plants are also described in for example WO 07/024,782.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084,082, for rice in WO 97/41218, for sugar beet in U.S. Pat. No. 5,773,702 and WO 99/057965, for lettuce in U.S. Pat. No. 5,198,599, or for sunflower in WO 01/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al. (1998, Microbiology and Molecular Biology Reviews, 62: 807-813), updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP 1999141 and WO 2007/107302); or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al. 2001, Nat. Biotechnol. 19: 668-72; Schnepf et al. 2006, Applied Environm. Microbiol. 71, 1765-1774) or the binary toxin made up of the Cry1A or Cry1F proteins and the Cry2Aa or Cry2Ab or Cry2Ae proteins (U.S. patent application Ser. No. 12/214,022 and EP 08010791.5); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON89034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or 9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. Patent Appl. No. 61/126,083 and 61/195,019), or the binary toxin made up of the VIP3 protein and the Cry2Aa or Cry2Ab or Cry2Ae proteins (U.S. patent application Ser. No. 12/214,022 and EP 08010791.5).

10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein)

Of course, an insect-resistant transgenic plant, as used herein, also includes any plant comprising a combination of genes encoding the proteins of any one of the above classes 1 to 10. In one embodiment, an insect-resistant plant contains more than one transgene encoding a protein of any one of the above classes 1 to 10, to expand the range of target insect species affected when using different proteins directed at different target insect species, or to delay insect resistance development to the plants by using different proteins insecticidal to the same target insect species but having a different mode of action, such as binding to different receptor binding sites in the insect.

An "insect-resistant transgenic plant", as used herein, further includes any plant containing at least one transgene comprising a sequence producing upon expression a double-stranded RNA which upon ingestion by a plant insect pest inhibits the growth of this insect pest, as described e.g. in WO 2007/080126.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

1) plants which contain a transgene capable of reducing the expression and/or the activity of poly(ADP-ribose) polymerase (PARP) gene in the plant cells or plants as described in WO 00/04173, WO/2006/045633, EP 04077984.5, or EP 06009836.5.

2) plants which contain a stress tolerance enhancing transgene capable of reducing the expression and/or the activity of the PARG encoding genes of the plants or plants cells, as described e.g. in WO 2004/090140.

3) plants which contain a stress tolerance enhancing transgene coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase as described e.g. in EP 04077624.7, WO 2006/133827, PCT/EP07/002,433, EP 1999263, or WO 2007/107326.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications. Said transgenic plants synthesizing a modified starch are disclosed, for example, in EP 0571427, WO 95/04826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, EP 06090134.5, EP 06090228.5, EP 06090227.7, EP 07090007.1, EP 07090009.7, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. No. 5,824,790, U.S. Pat. No. 6,013,861, WO 94/04693, WO 94/09144, WO 94/11520, WO 95/35026, WO 97/20936

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, as disclosed in EP 0663956, WO 96/01904, WO 96/21023, WO 98/39460, and WO 99/24593, plants producing alpha-1,4-glucans as disclosed in WO 95/31553, US 2002031826, U.S. Pat. No. 6,284,479, U.S. Pat. No. 5,712,107, WO 97/47806, WO 97/47807, WO 97/47808 and WO 00/14249, plants producing alpha-1,6 branched alpha-1,4-glucans, as disclosed in WO 00/73422, plants producing alternan, as disclosed in e.g. WO 00/47727, WO 00/73422, EP 06077301.7, U.S. Pat. No. 5,908,975 and EP 0728213, 3) transgenic plants which produce hyaluronan, as for example disclosed in WO 2006/032538, WO 2007/039314, WO 2007/039315, WO 2007/039316, JP 2006304779, and WO 2005/012529.

4) transgenic plants or hybrid plants, such as onions with characteristics such as 'high soluble solids content', 'low pungency' (LP) and/or 'long storage' (LS), as described in U.S. patent application Ser. No. 12/020,360 and 61/054,026.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:

a) Plants, such as cotton plants, containing an altered form of cellulose synthase genes as described in WO 98/00549 b) Plants, such as cotton plants, containing an altered form of rsw2 or rsw3 homologous nucleic acids as described in WO 2004/053219 c) Plants, such as cotton plants, with increased expression of sucrose phosphate synthase as described in WO 01/17333 d) Plants, such as cotton plants, with increased expression of sucrose synthase as described in WO 02/45485 e) Plants, such as cotton plants, wherein the timing of the plasmodesmatal gating at the basis of the fiber cell is altered, e.g. through downregulation of fiber-selective β-1,3-glucanase as described in WO 2005/017157, or as described in EP 08075514.3 or U.S. Patent Appl. No. 61/128,938 f) Plants, such as cotton plants, having fibers with altered reactivity, e.g. through the expression of N-acetylglucosaminetransferase gene including nodC and chitin synthase genes as described in WO 2006/136351

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics and include:

a) Plants, such as oilseed rape plants, producing oil having a high oleic acid content as described e.g. in U.S. Pat. No. 5,969,169, U.S. Pat. No. 5,840,946 or U.S. Pat. No. 6,323,392 or U.S. Pat. No. 6,063,947 b) Plants such as oilseed rape plants, producing oil having a low linolenic acid content as described in U.S. Pat. No. 6,270,828, U.S. Pat. No. 6,169,190 or U.S. Pat. No. 5,965,755 c) Plant such as oilseed rape plants, producing oil having a low level of saturated fatty acids as described e.g. in U.S. Pat. No. 5,434,283

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering as described in U.S. Patent Appl. No. 61/135,230 and EP 08075648.9.

Particularly useful transgenic plants which may be treated according to the invention are plants containing transformation events, or combination of transformation events, that are the subject of petitions for non-regulated status, in the United States of America, to the Animal and Plant Health Inspection Service (APHIS) of the United States Department of Agriculture (USDA) whether such petitions are granted or are still pending. At any time this information is readily available from APHIS (4700 River Road Riverdale, Md. 20737, USA), for instance on its internet site (URL http://www.aphis.usda.gov/brs/not_reg.html). On the filing date of this application the petitions for nonregulated status that were pending with APHIS or granted by APHIS were those listed in table B which contains the following information:

Petition: the identification number of the petition. Technical descriptions of the transformation events can be found in the individual petition documents which are obtainable from APHIS, for example on the APHIS website, by reference to this petition number. These descriptions are herein incorporated by reference.

Extension of Petition: reference to a previous petition for which an extension is requested.

Institution: the name of the entity submitting the petition.

Regulated article: the plant species concerned.

Transgenic phenotype: the trait conferred to the plants by the transformation event.

Transformation event or line: the name of the event or events (sometimes also designated as lines or lines) for which nonregulated status is requested.

APHIS documents: various documents published by APHIS in relation to the Petition and which can be requested with APHIS.

Additional particularly useful plants containing single transformation events or combinations of transformation events are listed for example in the databases from various national or regional regulatory agencies (see for example http://gmoinfo.jrc.it/gmp_browse.aspx and http://www.agbios.com/dbase.php).

Further particularly transgenic plants include plants containing a transgene in an agronomically neutral or beneficial position as described in any of the patent publications listed in Table C.

TABLE A

| Trait | Reference |
|---|---|
| Water use efficiency | WO 2000/073475 |
| Nitrogen use efficiency | WO 1995/009911 WO 2007/076115 |
| | WO 1997/030163 WO 2005/103270 |
| | WO 2007/092704 WO 2002/002776 |
| Improved photosynthesis | WO 2008/056915 WO 2004/101751 |
| Nematode resistance | WO 1995/020669 WO 2003/033651 |
| | WO 2001/051627 WO 1999/060141 |
| | WO 2008/139334 WO 1998/012335 |
| | WO 2008/095972 WO 1996/030517 |
| | WO 2006/085966 WO 1993/018170 |
| Reduced pod dehiscence | WO 2006/009649 WO 1997/013865 |
| | WO 2004/113542 WO 1996/030529 |
| | WO 1999/015680 WO 1994/023043 |
| | WO 1999/000502 |
| Aphid resistance | WO 2006/125065 WO 2008/067043 |
| | WO 1997/046080 WO 2004/072109 |
| *Sclerotinia* resistance | WO 2006/135717 WO 2005/000007 |
| | WO 2006/055851 WO 2002/099385 |
| | WO 2005/090578 WO 2002/061043 |
| Botrytis resistance | WO 2006/046861 WO 2002/085105 |
| *Bremia* resistance | US 20070022496 WO 2004/049786 |
| | WO 2000/063432 |
| *Erwinia* resistance | WO 2004/049786 |
| *Closterovirus* resistance | WO 2007/073167 WO 2002/022836 |
| | WO 2007/053015 |
| Stress tolerance (including drought tolerance) | WO 2010/019838 WO 2008/002480 |
| | WO 2009/049110 WO 2005/033318 |
| *Tobamovirus* resistance | WO 2006/038794 |

TABLE B

Petitions of Nonregulated Status Granted or Pending by APHIS as of Mar. 31, 2010

Applicant Documents

| Petition | Extension of Petition Number *** | Institution | Regulated Article | Transgenic Phenotype | Transformation Event or Line |
|---|---|---|---|---|---|
| *Petiotn for Nonregulated Status Pending* | | | | | |
| 10-070-01p | | Virginia Tech | Peanut | Sclerotinia blight resistant | N70, P39, and W171 |
| 09-349-01p | | Dow AgroSciences | Soybean | Herbicide Tolerant | DAS-68416-4 |
| 09-328-01p | | Bayer Crop Science | Soybean | Herbicide Tolerant | FG72 |
| 09-233-01p | | Dow | Corn | Herbicide Tolerant | DAS-40278-9 |
| 09-201-01p | | Monsanto | Soybean | | MON-87705-6 |
| 09-183-01p | | Monsanto | Soybean | | MON-87769 |
| 09-082-01p | | Monsanto | Soybean | Lepidopteran resistant | MON 87701 |
| 09-063-01p | | Stine Seed | Corn | Glyphosate tolerant | HCEM485 |
| 09-055-01p | | Monsanto | Corn | Drought Tolerant | MON 87460 |
| 09-015-01p | | BASF Plant Science, LLC | Soybean | Herbicide Tolerant | BPS-CV127-9 Soybean |
| 08-366-01p | | ArborGen | *Eucalyptus* | Freeze Tolerant, Fertility Altered | ARB-FTE1-08 |
| 08-340-01p | | Bayer | Cotton | Glufosinate Tolerant, Insect Resistant | T304-40XGHB119 |
| 08-338-01p | | Pioneer | Corn | Male Sterile, Fertility Restored, Visual Marker | DP-32138-1 |
| 08-315-01p | | Florigene | Rose | Altered Flower Color | IFD-52401-4 and IFD-52901-9 |
| 07-253-01p | | Syngenta | Corn | Lepidopteran resistant | MIR-162 Maize |
| 07-108-01p | | Syngenta | Cotton | Lepidopteran Resistant | COT67B |
| 06-354-01p | | Pioneer | Soybean | High Oleic Acid | DP-305423-1 |
| 05-280-01p | | Syngenta | Corn | Thermostable alpha-amylase | 3272 |
| 04-110-01p | | Monsanto & Forage Genetics | Alfalfa | Glyphosate Tolerant | J101, J163 |
| 03-104-01p | | Monsanto & Scotts | Creeping bentgrass | Glyphosate Tolerant | ASR368 |
| *Petitions for Nonregulated Status Granted* | | | | | |
| 07-152-01p | | Pioneer | Corn | glyphosate & Imidazolinone tolerant | DP-098140-6 |
| 04-337-01p | | University of Florida | Papaya | *Papaya Ringspot Virus* Resistant | X17-2 |
| 06-332-01p | | Bayer CropScience | Cotton | Glyphosate tolerant | GHB614 |
| 06-298-01p | | Monsanto | Corn | European Corn Borer resistant | MON 89034 |
| 06-271-01p | | Pioneer | Soybean | Glyphosate & acetolactate synthase tolerant | 356043 (DP-356043-5) |

TABLE B-continued

Petitions of Nonregulated Status Granted or Pending by APHIS as of Mar. 31. 2010

Applicant Documents

| Petition | Extension of Petition Number *** | Institution | Regulated Article | Transgenic Phenotype | Transformation Event or Line |
|---|---|---|---|---|---|
| 06-234-01p | 98-329-01p | Bayer CropScience | Rice | Phosphinothrcin tolerant | LLRICE601 |
| 06-178-01p | | Monsanto | Soybean | Glyphosate tolerant | MON 89788 |
| 04-362-01p | | Syngenta | Corn | Corn Rootworm Protected | M1R604 |
| 04-264-01p | | ARS | Plum | Plum Pox Virus Resistant | C5 |
| 04-229-01p | | Monsanto | Corn | High Lysine | LY038 |
| 04-125-01p | | Monsanto | Corn | Corn Rootworm Resistant | 88017 |
| 04-086-01p | | Monsanto | Cotton | Glyphosate Tolerant | MON 88913 |
| 03-353-01p | | Dow | Corn | Corn Rootworm Resistant | 59122 |
| 03-323-01p | | Monsanto | Sugar Beet | Glyphosate Tolerant | H7-1 |
| 03-181-01p | 00-136-01p | Dow | Corn | Lepidopteran Resistant & Phosphinothricin tolerant | TC-6275 |
| 03-155-01p | | Syngenta | Cotton | Lepidopteran Resistant | COT 102 |
| 03-036-01p | | Mycogen/Dow | Cotton | Lepidopteran Resistant | 281-24-236 |
| 03-036-02p | | Mycogen/Dow | Cotton | Lepidopteran Resistant | 3006-210-23 |
| 02-042-01p | | Aventis | Cotton | Phosphinothericin tolerant | LLCotton25 |
| 01-324-01p | 98-216-01p | Monsanto | Rapeseed | Glyphosate tolerant | RT200 |
| 01-206-01p | 98-278-01p | Aventis | Rapeseed | Phosphinothricin tolerant & pollination control | MS1 & RF1/RF2 |
| 01-206-02p | 97-205-01p | Aventis | Rapeseed | Phosphinothricin tolerant | Topas 19/2 |
| 01-137-01p | | Monsanto | Corn | Corn Rootworm Resistant | MON 863 |
| 01-121-01p | | Vector | Tobacco | Reduced nicotine | Vector 21-41 |
| 00-342-01p | | Monsanto | Cotton | Lepidopteran resistant | Cotton Event 15985 |
| 00-136-01p | | Mycogen c/o Dow & Pioneer | Corn | Lepidopteran resistant phosphinothricin tolerant | Line 1507 |
| 00-011-01p | 97-099-01p | Monsanto | Corn | Glyphosate tolerant | NK603 |
| 99-173-01p | 97-204-01p | Monsanto | Potato | PLRV & CPB resistant | RBMT22-82 |
| 98-349-01p | 95-228-01p | AgrEvo | Corn | Phosphinothricin tolerant and Male sterile | MS6 |
| 98-335-01p | | U. of Saskatchewan | Flax | Tolerant to soil residues of sulfonyl urea herbicide | CDC Triffid |
| 98-329-01p | | AgrEvo | Rice | Phosphinothricin tolerant | LLRICE06, LLRICE62 |
| 98-278-01p | | AgrEvo | Rapeseed | Phosphinothricin tolerant & Pollination control | MS8 & RF3 |
| 98-238-01p | | AgrEvo | Soybean | Phosphinothricin tolerant | GU262 |
| 98-216-01p | | Monsanto | Rapeseed | Glyphosate tolerant | RT73 |
| 98-173-01p | | Novartis Seeds & Monsanto | Beet | Glyphosate tolerant | GTSB77 |
| 98-014-01p | 96-068-01p | AgrEvo | Soybean | Phosphinothricin tolerant | A5547-127 |
| 97-342-01p | | Pioneer | Corn | Male sterile & Phosphinothricin tolerant | 676, 678, 680 |
| 97-339-01p | | Monsanto | Potato | CPB & PVY resistant | RBMT15-101, SEMT15-02, SEMT15-15 |
| 97-336-01p | | AgrEvo | Beet | Phosphinothricin tolerant | T-120-7 |
| 97-287-01p | | Monsanto | Tomato | Lepidopteran resistant | 5345 |
| 97-265-01p | | AgrEvo | Corn | Phosphinothricin tolerant & Lep. resistant | CBH-351 |
| 97-205-01p | | AgrEvo | Rapeseed | Phosphinothricin tolerant | T45 |
| 97-204-01p | | Monsanto | Potato | CPB & PLRV resistant | RBMT21-129 & RBMT21-350 |
| 97-148-01p | | Bejo | *Cichorium intybus* | Malesterile | RM3-3, RM3-4, RM3-6 |
| 97-099-01p | | Monsanto | Corn | Glyphosate tolerant | GA21 |
| 97-013-01p | | Calgene | Cotton | Bromoxynil tolerant & Lepidopteran resistant | Events 31807 & 31808 |
| 97-008-01p | | Du Pont | Soybean | Oil profile altered | G94-1, G94-19, G-168 |
| 96-317-01p | | Monsanto | Corn | Glyphosate tolerant & ECB resistant | MON802 |
| 96-291-01p | | DeKalb | Corn | European Corn Borer resistant | DBT418 |
| 96-248-01p | 92-196-01p | Calgene | Tomato | Fruit ripening altered | 1 additional FLAVRSAVR line |
| 96-068-01p | | AgrEvo | Soybean | Phosphinothricin tolerant | W62, W98, A2704- 12, A2704-21, A5547-35 |
| 96-051-01p | | Cornell U | Papaya | PRSV resistant | 55-1, 63-1 |
| 96-017-01p | 95-093-01p | Monsanto | Corn | European Corn Borer resistant | MON809 & MON810 |
| 95-352-01p | | Asgrow | Squash | CMV, ZYMV, WMV2 resistant | CZW-3 |
| 95-338-01p | | Monsanto | Potato | CPB resistant | SBT02-5 & −7, ATBT04-6 & −27, −30, −31, −36 |
| 95-324-01p | | Agritope | Tomato | Fruit ripening altered | 35 1 N |
| 95-256-01p | | Du Pont | Cotton | Sulfonylurea tolerant | 19-51a |

TABLE B-continued

Petitions of Nonregulated Status Granted or Pending by APHIS as of Mar. 31, 2010

Applicant Documents

| Petition | Extension of Petition Number *** | Institution | Regulated Article | Transgenic Phenotype | Transformation Event or Line |
|---|---|---|---|---|---|
| 95-228-01p | | Plant Genetic Systems | Corn | Male sterile | MS3 |
| 95-195-01p | | Northrup King | Corn | European Corn Borer resistant | Btl 1 |
| 95-179-01p | 92-196-01p | Calgene | Tomato | Fruit ripening altered | 2 additional FLAVRSAVR lines |
| 95-145-01p | | DeKalb | Corn | Phosphinothricin tolerant | B16 |
| 95-093-01p | | Monsanto | Corn | Lepidopteran resistant | MON 80100 |
| 95-053-01p | | Monsanto | Tomato | Fruit ripening altered | 8338 |
| 95-045-01p | | Monsanto | Cotton | Glyphosate tolerant | 1445, 1698 |
| 95-030-01p | 92-196-01p | Calgene | Tomato | Fruit ripening altered | 20 additional FLAVRSAVR lines |
| 94-357-01p | | AgrEvo | Corn | Phosphinothricin tolerant | T14, T25 |
| 94-319-01p | | Ciba Seeds | Corn | Lepidopteran resistant | Event 176 |
| 94-308-01p | | Monsanto | Cotton | Lepidopteran resistant | 531, 757, 1076 |
| 94-290-01p | | Zeneca & Petoseed | Tomato | Fruit polygalacturonase level decreased | B, Da, F |
| 94-257-01p | | Monsanto | Potato | Coleopteran resistant | BT6, BT10, BT12, BT16, BT17, BT18, BT23 |
| 94-230-01p | 92-196-01p | Calgene | Tomato | Fruit ripening altered | 9 additional FLAVRSAVR lines |
| 94-228-01p | | DNA Plant Tech | Tomato | Fruit ripening altered | 1345-4 |
| 94-227-01p | 92-196-01p | Calgene | Tomato | Fruit ripening altered | Line N73 1436-111 |
| 94-090-01p | | Calgene | Rapeseed | Oil profile altered | pCGN3828-212/86-18 & 23 |
| 93-258-01p | | Monsanto | Soybean | Glyphosate tolerant | 40-3-2 |
| 93-196-01p | | Calgene | Cotton | Bromoxynil tolerant | BXN |
| 92-204-01p | | Upjohn | Squash | WMV2 & ZYMV resistant | ZW-20 |
| 92-196-01p | | Calgene | Tomato | Fruit ripening altered | FLAVR SAVR |

NOTE:
To obtain the most up-to-date list of Crops No Longer Regulated, please look at the Current Status of Petitions. This list is automatically updated and reflects all petitions received to date by APHIS, including petitions pending, withdrawn, or approved.
Abbreviations:
CMV-cucumber mosaic virus;
CPB-colorado potato beetle;
PLRV-potato leafroll virus;
PRSV-papaya ringspot virus;
PVY-potato virus Y;
WMV2-watermelon mosaic virus 2
ZYMV-zucchini yellow mosaic virus
*** Extension of Petition Number: Under 7CFR 340.6(e) a person may request that APHIS extend a determination of non-regulated status to other organisms based on their similarity of the previously deregulated article. This column lists the previously granted petition of that degregulated article.
**** Preliminary EA: The Environmental Assessment initially available for Public comment prior to finalization.

TABLE C

| Plant species | Event | Trait | Patent reference |
|---|---|---|---|
| Corn | PV-ZMGT32 (NK603) | Glyphosate tolerance | US 2007-056056 |
| Corn | MIR604 | Insect resistance (Cry3a055) | EP 1 737 290 |
| Corn | LY038 | High lysine content | U.S. Pat. No. 7,157,281 |
| Corn | 3272 | Self processing corn (alpha-amylase) | US 2006-230473 |
| Corn | PV-ZMIR13 (MON863) | Insect resistance (Cry3Bb) | US 2006-095986 |
| Corn | DAS-59122-7 | Insect resistance (Cry34Ab1/Cry35Ab1) | US 2006-070139 |
| Corn | TC1507 | Insect resistance (Cry1F) | U.S. Pat. No. 7,435,807 |
| Corn | MON810 | Insect resistance (Cry1Ab) | US 2004-180373 |
| Corn | VIP1034 | Insect resistance | WO 03/052073 |
| Corn | B16 | Glufosinate resistance | US 2003-126634 |
| Corn | GA21 | Glyphosate resistance | U.S. Pat. No. 6,040,497 |
| Corn | GG25 | Glyphosate resistance | U.S. Pat. No. 6,040,497 |
| Corn | GJ11 | Glyphosate resistance | U.S. Pat. No. 6,040,497 |
| Corn | FI117 | Glyphosate resistance | U.S. Pat. No. 6,040,497 |
| Corn | GAT-ZM1 | Glufosinate tolerance | WO 01/51654 |
| Corn | MON87460 | Drought tolerance | WO 2009/111263 |
| Corn | DP-098140-6 | Glyphosate tolerance/ALS inhibitor tolerance | WO 2008/112019 |

TABLE C-continued

| Plant species | Event | Trait | Patent reference |
|---|---|---|---|
| Wheat | Event 1 | *Fusarium* resistance (trichothecene 3-O-acetyltra nsferase) | CA 2561992 |
| Sugar beet | T227-1 | Glyphosate tolerance | US 2004-117870 |
| Sugar beet | H7-1 | Glyphosate tolerance | WO 2004-074492 |
| Soybean | MON89788 | Glyphosate tolerance | US 2006-282915 |
| Soybean | A2704-12 | Glufosinate tolerance | WO 2006/108674 |
| Soybean | A5547-35 | Glufosinate tolerance | WO 2006/108675 |
| Soybean | DP-305423-1 | High oleic acid/ALS inhibitor tolerance | WO 2008/054747 |
| Rice | GAT-OS2 | Glufosinate tolerance | WO 01/83818 |
| Rice | GAT-OS3 | Glufosinate tolerance | US 2008-289060 |
| Rice | PE-7 | Insect resistance (Cry1Ac) | WO 2008/114282 |
| Oilseed rape | MS-B2 | Male sterility | WO 01/31042 |
| Oilseed rape | MS-BN1/RF-BN1 | Male sterility/restoration | WO 01/41558 |
| Oilseed rape | RT73 | Glyphosate resistance | WO 02/36831 |
| Cotton | CE43-67B | Insect resistance (Cry1Ab) | WO 2006/128573 |
| Cotton | CE46-02A | Insect resistance (Cry1Ab) | WO 2006/128572 |
| Cotton | CE44-69D | Insect resistance (Cry1Ab) | WO 2006/128571 |
| Cotton | 1143-14A | Insect resistance (Cry1Ab) | WO 2006/128569 |
| Cotton | 1143-51B | Insect resistance (Cry1Ab) | WO 2006/128570 |
| Cotton | T342-142 | Insect resistance (Cry1Ab) | WO 2006/128568 |
| Cotton | event3006-210-23 | Insect resistance (Cry1Ac) | WO 2005/103266 |
| Cotton | PV-GHGT07 (1445) | Glyphosate tolerance | US 2004-148666 |
| Cotton | MON88913 | Glyphosate tolerance | WO 2004/072235 |
| Cotton | EE-GH3 | Glyphosate tolerance | WO 2007/017186 |
| Cotton | T304-40 | Insect-resistance (Cry1Ab) | WO 2008/122406 |
| Cotton | Cot202 | Insect resistance (VIP3) | US 2007-067868 |
| Cotton | LLcotton25 | Glufosinate resistance | WO 2007/017186 |
| Cotton | EE-GH5 | Insect resistance (Cry1Ab) | WO 2008/122406 |
| Cotton | event 281-24-236 | Insect resistance (Cry1F) | WO 2005/103266 |
| Cotton | Cot102 | Insect resistance (Vip3A) | US 2006-130175 |
| Cotton | MON 15985 | Insect resistance (Cry1A/Cry2Ab) | US 2004-250317 |
| Bent Grass | Asr-368 | Glyphosate tolerance | US 2006-162007 |
| Brinjal | EE-1 | Insect resistance (Cry1Ac) | WO 2007/091277 |

When the composition according to the invention comprises a strigolactone derivative of formula (I) or (II), a lipo-chitooligosaccharide compound, and a pesticidal active material, the dose of active material usually applied is generally and advantageously between 0.00001 and 1000 g/ha, preferably between 0.0001 and 500 g/ha for applications in foliar treatment. If a drench/drip/in furrow application is possible, the dose can be lower, especially in artificial substrates like rockwool or perlite. The dose of active substance applied is generally and advantageously between 0.000001 and 200 g per 100 kg of seed, preferably between 0.00001 and 150 g per 100 kg of seed in the case of seed treatment. It is clearly understood that the doses indicated above are given as illustrative examples of the invention. A person skilled in the art will know how to adapt the application doses according to the nature of the crop to be treated.

EXAMPLES

1. Greenhouse Experiments on Soybean

Test is performed in the greenhouse. 5 soybean seeds per treatment of the variety Cordoba were sown in 500 ml rose pots (7×7×18 cm) containing a mix of sand and perlite (1:1). 3 replicates were made. The active ingredient was solved in a solvent and seed treatment was performed with a lab equipment.

To inoculate with arbuscular mycorrhizal fungi, 10 g inoculum (Vaminoc; MicroBio Ltd.) were mixed with 1 l of the sand-perlite mixture.

Seeds were covered by 3 cm of LECA (light expanded clay aggregate). Pots were incubated in the greenhouse for 6 weeks at 22° C./15° C. (day/night) and 80% relative humidity. Assessment consisted of root weight and leaf area.

Compound A1:

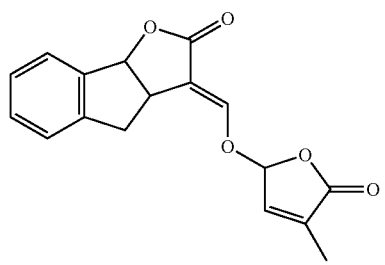 [SMILES: CC1=CC(O/C=C2/C(=O)OC3c4ccccc4CC23)OC1=O]

Compound B1:

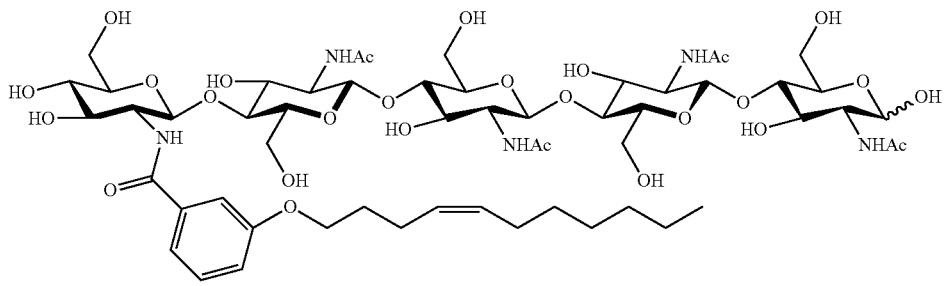

| | Leaf Area [cm$^2$] | Root weight [g] |
|---|---|---|
| B1 | 36.82 | 9.19 |
| A1 | 35.67 | 11.13 |
| B1 + A1 | 44.67 | 12.15 |
| B1 + A1 | 23.02 | 16.9 |
| Prothioconazole | 20.58 | 16.8 |
| B1 + A1 + Prothioconazole | 27.42 | 18.2 |
| Trifloxystrobin | 24.80 | 18.2 |
| B1 + A1 + Trifloxystrobin | 26.17 | 19.1 | average of 3 replicates of 5 plants

The combination A1+B1 applied on soybean seeds demonstrates a significative increase of the biomass (root+leaf), particularly leaf, comparatively to compound A1 and B1 when applied separately. Said beneficial effect is even significatively increased by the addition of fungicides to the combination A1+B1 comparatively to fungicides and (A1+B1) when applied separately.

2. Germination Test on Wheat and Soybean

Test is performed in a climate chamber. 20 soybean seeds per treatment of the variety Cordoba were sown on agar plates (0.8% agar). 5 replicates were made. The active ingredient was solved in a solvent and seed treatment was performed with a lab equipment. Plates were incubated at 10° C. in darkness. After 4 days the germination rate and root length were assessed.

For wheat experiments 20 wheat seeds per treatment of the variety Tuareg were sown on agar plates (1.4% agar). 5 replicates were made. The active ingredient was solved in a solvent and seed treatment was performed with a lab equipment. Plates were incubated at 10° C. in darkness. After 2 days the germination rate and root length were assessed.

Compound A1:

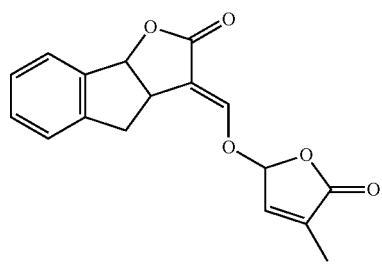

Compound B1:

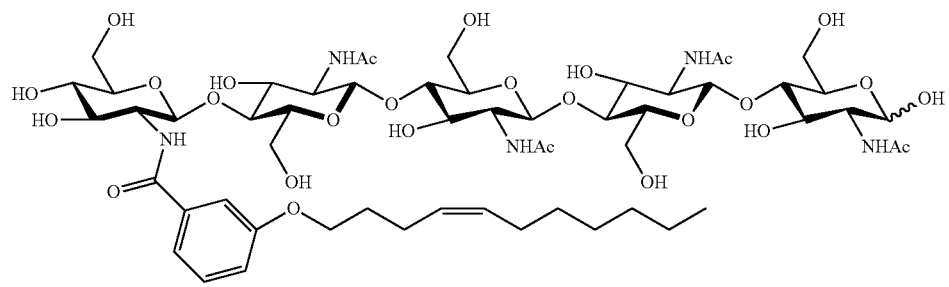

-continued
Compound B2:
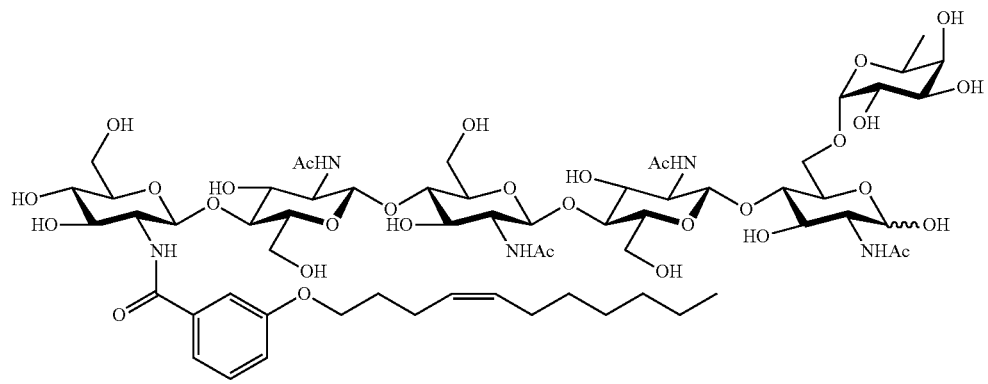
Compound B3:
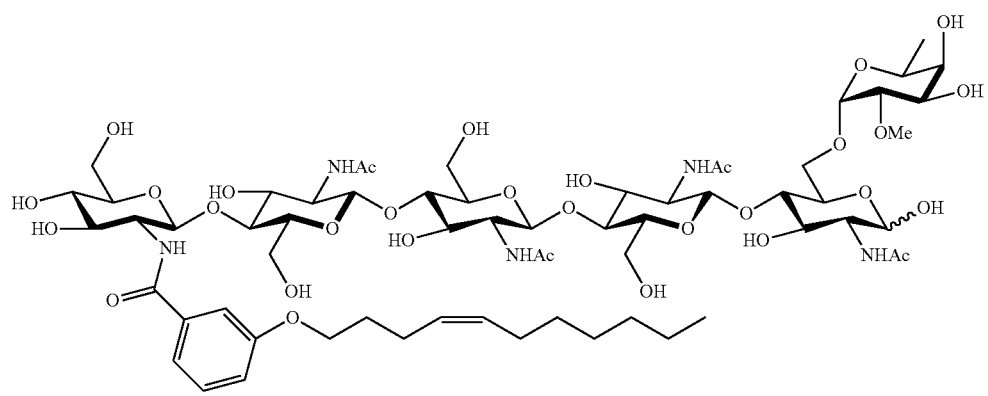
Compound B4:
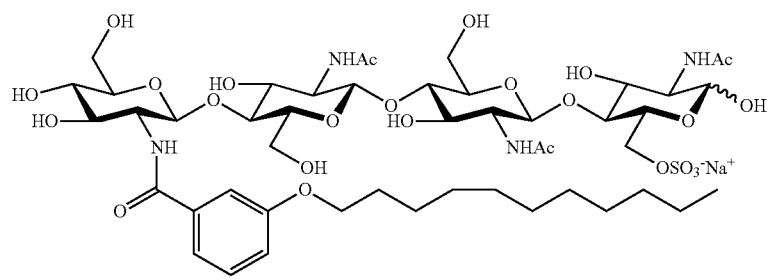
|  | Germination rate [%] | Root length [cm] |
|---|---|---|
| Wheat | | |
| A1 | 27 | 3.04 |
| B2 | 18 | 2.02 |
| B3 | 17 | 2.18 |
| B1 | 8 | 2.34 |
| A1 + B2 | 35 | 3.81 |
| A1 + B3 | 26 | 3.71 |
| A1 + B1 | 38 | 3.70 |
| Soybean | | |
| A1 | 63 | 5.19 |
| B4 | 68 | 5.61 |
| B2 | 68 | 5.61 |
| B3 | 59 | 5.13 |
| B1 | 58 | 5.64 |
| A1 + B4 | 81 | 6.45 |
| A1 + B2 | 76 | 6.00 |
| A1 + B3 | 74 | 5.44 |
| A1 + B1 | 84 | 5.91 | average of 5 replicates of 20 seeds

The combinations A1+B1, A1+B2 applied on wheat seeds demonstrates a significative increase of the germination rate and root length, comparatively to compound A1, B1 and B2 when applied separately. The combinations A1+B3 applied on wheat seeds demonstrates an increase of the root length, comparatively to compound A1 and B3 when applied separately. The combinations A1+B1, A1+B2, A1+B3, A1+B4 applied on soybean seeds demonstrates a significative increase of the germination rate and root length, comparatively to compound A1, B1, B2, B3 and B4 when applied separately.

3. Corn, Wheat and Soybean Field Trials (2008/2009/2010)

Corn, wheat and soybean field trials were conducted to evaluate the effect of strigolactone compounds, of LCO compounds, of compositions comprising a strigolactone compound and a LCO compound on several assessments including the weight of plant (leaf+roots), the formation of nodules, and yield parameters like the weight of grains per plot, Decitons per ha, the 1000 kernels weight. A base made up of fungicides & insecticides is also applied on the seeds, in addition to the strigolactone compounds, LCO compounds, or strigolactone+LCO compounds.

The strigolactone compound A1 and the LCO compound B1 and were prediluted in mixture water+aceton and applied on seeds in tank mix with Fungicides and Insecticides.

Corn: trial code FA09DVG55F225 Germany (Mettmann), soil description, loamy sand, % sand 60.2, % silt 29.2, % clay 10.6, % organic matter 1.5, Ph 6.6. Sowing date: May Corn: trial code FA09WLDM02PL31 Frace (Poumarede), soil description, clayey silt, % sand 25.8, % silt 58.4, % clay 14.2, % organic matter 1.6, Ph 6.5. Sowing date May;

Corn: trial code FA09VSIA333MJ1 Italy (Bologna), soil description: sandy silt, % sand 45, % silt 37, % clay 18, % organic matter 1.91, Ph 8.19. Sowing date May;

Winter wheat: trial code FA09DVG040F175 Germany (Voiswinkel), soil description: loamy sand, % sand 55.3, % silt 33.7, % clay 11, % organic matter 1.5, Ph 6.5. Sowing date: November Soybean: trial code FA09NARR12UHG1 USA (MS), soil description: sandy loam, % sand 35, % silt 55, % clay 9, % organic matter 0.6, Ph 6.6. Sowing date: May 21

Dosages Corn:

Compound B1: 0.5 milligrams active ingredient per hundret kilograms seed

Compound A1: 5 milligrams active ingredient per hundret kilograms seed

Base: Fungicide: Prothioconazole+Metalaxyl FS 120/Dosage: 0.03+0.006 milligrams active ingredient per seed, Insecticide: Poncho 600 FS 600 (Clothianidin)/Dosage: 0.50 milligrams active ingredient per seed.

Dosages Soybean:

Compound B1: 0.15 milligrams active ingredient per hundret kilograms seed

Compound A1:

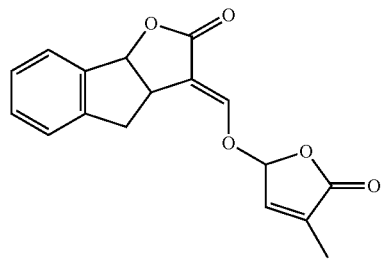

Compound B1:

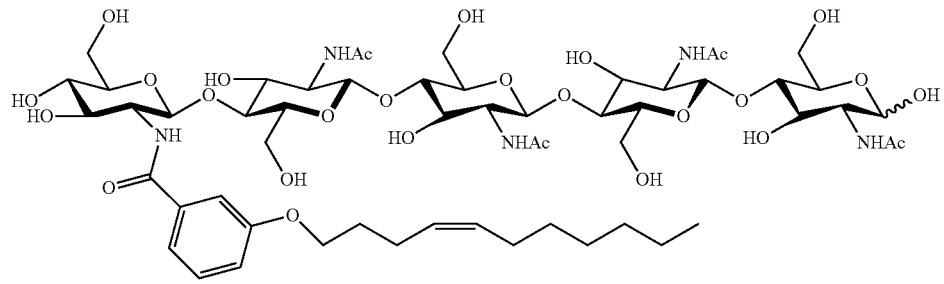

Several trials on different sites (France, Spain, Italy, Germany and USA) have been performed, including trials in non-optimum soil, e.g. low Ph, organic matter weak. Description of trial conditions and results are given below.

a) Field trials 1:

Corn: trial code FA09VSSAM01 Spain (Sevilla), soil description: clay loam, % sand 38, % silt 38, % clay 24, % organic matter 1.16, Ph: 8.24. Sowing date: April Corn: trial code FA09VSFM01PL29 France (Finhan), soil description: loamy sand, % sand 23.9, % silt 60.4, % clay 14.5, organic matter 1.3, Ph 5.3. Sowing date: May Compound A1: 1.5 milligrams active ingredient per hundret kilograms seed Base: Fungicide: Trilex Allegiance FS 138.5: Trifloxystrobin+Metalaxyl/Dosage 5+4 grams active ingredient per hundret kilograms seed; Insecticide: Gaucho 600 FS 600: Imidacloprid/Dosage: 62.5 grams active ingredient per kilograms seed.

Dosages Winter Wheat:

Compound B1: 0.058 milligrams active ingredient per hundret kilograms seed

Compound A1: 0.58 milligrams active ingredient per hundret kilograms seed
Base: Fungicide: Fluoxastrobin+Prothioconazole+Tebuconazole FS 80/dosage: 5.6+5.6+0.747 grams active ingredient per hundret kilograms seed.

The following parameters were assessed:
weight of plant (leaf+roots), 6 weeks after sowing for Corn and Soybean, 4 months after sowing for Winter Wheat (Spring). 15 plants per plot were pulled out, washed and weighed.
Count on soybean number of nodules per plant. 10 plants per plot were pulled out per plot.
Yield parameters: weight of grains per plot, Decitons per ha calculated, TWG=1000 kernels weight.

Dosages Winter Wheat (Bergisches Land):
Compound B1: 0.06 mg/100 kg
Compound A1: 0.6 mg/100 kg
Base: Insecticide (I): Imidacloprid; Fungicides (F): Fluoxastrobin & Tebuconazole & Prothioconazole.

TABLE 2

Results: Winter wheat (Bergisches Land):

|  | TKW in g | Hectoliter in hl | Yield in dt/ha |
|---|---|---|---|
| F + I | 32.7 | 72.7 | 12 |
| F + I + B1 | 33.0 | 72.8 | 16 |

TABLE 1

Results:

| Plant | Corn | Corn | Winter wheat | Soybean |
|---|---|---|---|---|
| Location | Spain site 1 brenes | France Finhan | Germany Voiswinkel | US MS |
| Trial | FA09VSSM2SAM01 | FA09VSFM01PL29 | FA09DVG040F175 | FA09NARRI2UHG1 |
| Assessment | root + leaf plant weight in gram 10 plants Stage BBCH18 average/3 replicates | root + leaf plant weight in gram 10 plants Stage BBCH16 average/3 replicates | root + leaf plant weight in gram 15 plants Stage BBCH30 average/3 replicates | Nodules Number 5 plants Stage BBCH20 average/3 replicates |
| Base = B | 80.8 | 51.44 | 13.53 | 32.3 |
| B + A1 | 118.5 | 60.04 | 12.95 | 44.3 |
| B + B1 | 109.3 | 68.67 | 14.43 | 43.3 |
| B + A1 + B1 | 122.5 | 82.79 | 18.55 | 54.3 |
| LSD (P = 0.05) | 45.82 | 45.14 | 5.917 | 13.66 |
| Standard deviation | 28.1 | 28.222 | 3.699 | 8.54 |
| coef of variation | 26.08 | 42.93 | 24.89 | 19.63 |

| Plant | Corn | Corn | Corn | Soybean |
|---|---|---|---|---|
| Location | Germany Mettman | Italy Bologna | France Poumarede | US MS |
| Trial | FA09DVG55F225 | FA09VSIA333MJ1 | FA0VSFM02PL31 | FA09NARRI2UHG1 |
| Assessment | Yield Dt ha harvest 3 replicates average/3 replicates | Yield TKW 1000 kernel harvest 3 replicates average/3 replicates | Yield Dt ha harvest 3 replicates average/3 replicates | yield kg ha Harvest 3 replicates average/3 replicates |
| Base = B | 122.8 | 353.5 | 67.5 | 5136.7 |
| B + A1 | 117 | 366.3 | 78.6 | 5340.2 |
| B + B1 | 110 | 359a | 83.1 | 5346.5 |
| B + A1 + B1 | 126.3 | 372.3 | 85.1 | 5734.3 |
| LSD (P = 0.05) | 14.79 | 10.44 | 13.44 | 728.22 |
| Standard deviation | 9.6 | 7.23 | 8.41 | 455.28 |
| coefficient of variation | 8.08 | 2.01 | 10.7 | 8.45 |

The combination A1 + B1 applied on seed demonstrates a significative increase of the biomass (root + leaf) on Corn and Winter wheat comparatively to compound A1 and B1 when applied separately.
The combination A1 + B1 increases significantly the number of nodules (measured on roots) in the trial conducted in US on Soybean.
The combination A1 + B1 increases the yield (deciton per ha, or kg per ha) on Corn and on Soybean.
An increase of the TKW (1000 kernels weight) was also observed on Corn.

b) Field trials 2: Winter wheat: Germany (Bergisches Land):

Seeds of the variety "Dekan" were planted on December with a seed density of 400 seeds/m$^2$ on a non-fertilized soil. The plot size was 6 m×2.5 m (=15 m$^2$) and four randomised replicates were used. The application of plant protection products were carried out according to the good agricultural practise. The evaluation of different growth parameters was done during the season.

TABLE 2-continued

Results: Winter wheat (Bergisches Land):

|  | TKW in g | Hectoliter in hl | Yield in dt/ha |
|---|---|---|---|
| F + I + A1 | 33.6 | 72.6 | 16 |
| F + I + A1 + B1 | 34.9 | 73.8 | 23 |

The results showed that the treatments with B1, A1, B1+A1 resulted in an increased yield in dt/ha in comparison to the untreated control. Especially the treatment B1+A1 outperformed the other treatments and a synergistic effect between B1 and A1 was clearly visible.

The invention claimed is:

1. A synergistic composition comprising:

a) a compound of formula (Ia)

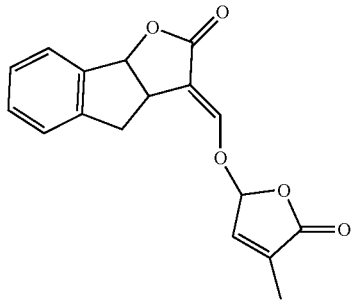

(Ia)

and b) a lipo-chitooligosaccharide compound selected from the group consisting of:

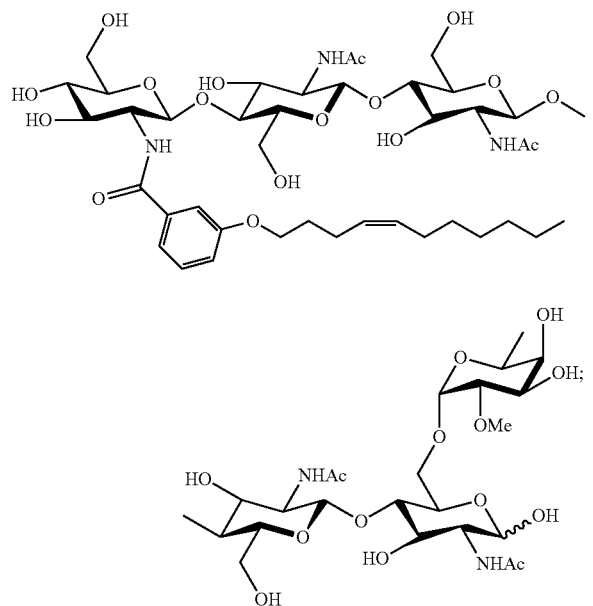

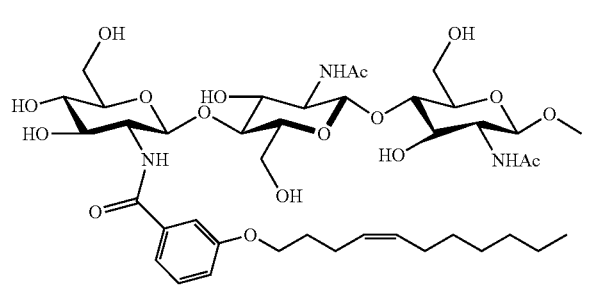

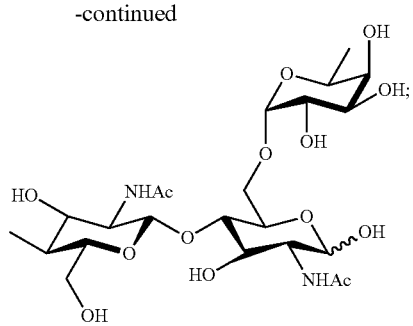

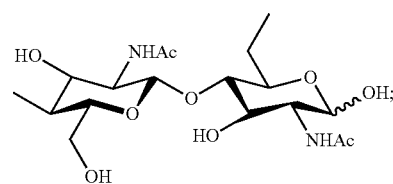

and

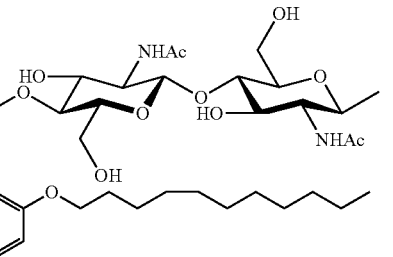

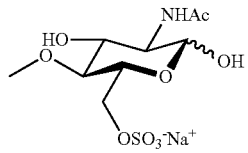

in a (a)/(b) weight ratio of from 0.05 to 100.

2. A composition according to claim 1, further comprising a pesticidal active ingredient.

3. A composition according to claim 2, wherein the pesticidal active ingredient is a fungicide, insecticide, nematicide, acaricide or molluscicide compound.

4. A composition according to claim 1, wherein it further comprises an agriculturally acceptable support, carrier, filler and/or surfactant.

5. A composition according to claim 1, wherein it further comprises a supplementation with Arbuscular mycorrhizal fungi, *rhizobia* or plant growth promoting bacteria.

6. A composition according to claim 5 wherein the Arbuscular mycorrhizae fungi are from the group Glomeromycota, particularly *Glomus* sp., or *Gigaspora* sp., or the bacteria are *Rhizobia* sp., *Azospirillium* sp. or *Bacillus* sp.

7. A method for improving the plant growth and/or increasing the yield of leguminous or non-leguminous plant or crop, and/or decreasing the need for fertilizers, wherein an effective and non-phytotoxic amount of a composition according to claim 1 is applied via seed treatment, foliar application, stem application, drench/drip application (chemigation) to the seed, the plant or to the fruit of the plant or to soil or to inert substrate, Pumice, Pyroclastic materials/tuff, synthetic organic substrates, organic substrates or to a liquid substrate in which the plant is growing or in which it is desired to grow.

8. A method for curatively or preventively controlling phytopathogenic fungi of crops wherein an effective and non-phytotoxic amount of a composition according to claim 1 is applied via seed treatment, foliar application, stem application, drench/drip application (chemigation) to the seed, the plant or to the fruit of the plant or to soil or to inert substrate, Pumice, Pyroclastic materials/tuff, synthetic organic substrates, organic substrates or to a liquid substrate in which the plant is growing or in which it is desired to grow.

9. A method according to claim 7, wherein the composition is applied in furrow on the soil.

10. The use of the composition as claimed in claim 1 for improving the plant growth and/or increasing the yield of leguminous or non-leguminous plant or crop, and/or decreasing the need for fertilizers with the step of:
applying an effective amount of the composition via any of seed treatment, foliar applications, stem application, drench/drip application to any of a seed, a plant, a fruit, soil or to inert substrate, pumice, pyroclast materials/turf, synthetic organic substrates, organic substrates or liquid substrate in which the plant is growing or in which it is desired to grow.

11. The use of the composition as claimed in claim 1 for curatively or preventively controlling phytopathogenic fungi with the step of:
applying an effective amount of the composition via any of seed treatment, foliar applications, stem application, drench/drip application to any of a seed, a plant, a fruit, soil or to inert substrate, pumice, pyroclast materials/turf, synthetic organic substrates, organic substrates or liquid substrate in which the plant is growing or in which it is desired to grow.

12. The use of the composition as claimed in claim 1 for curatively or preventively controlling phytopathogenic insects with the step of:
applying an effective amount of the composition via any of seed treatment, foliar applications, stem application, drench/drip application to any of a seed, a plant, a fruit, soil or to inert substrate, pumice, pyroclast materials/turf, synthetic organic substrates, organic substrates or liquid substrate in which the plant is growing or in which it is desired to grow.

13. A composition according to claim 1, wherein the lipo-chitooligosaccharide compound is

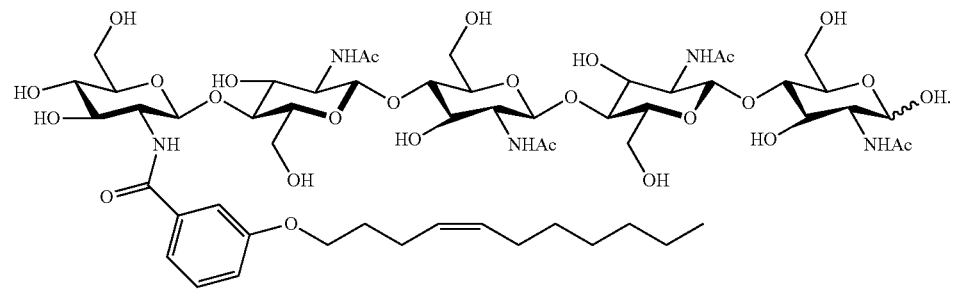

14. A composition according to claim 1, wherein the lipo-chitooligosaccharide compound is

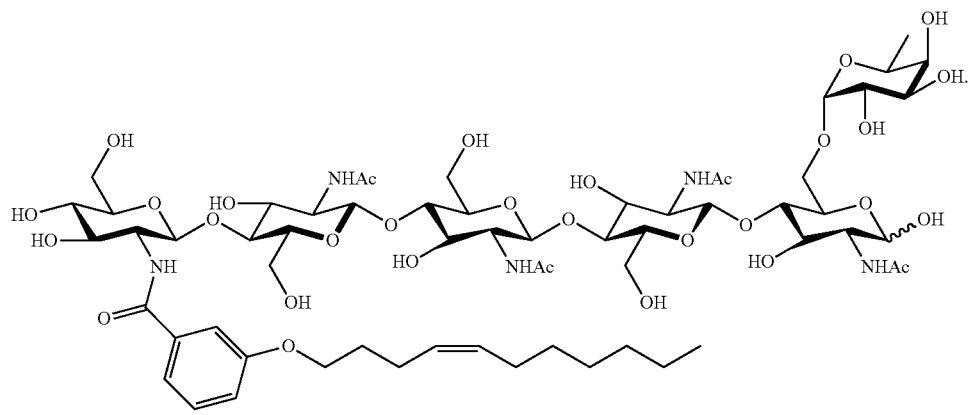

15. A composition according to claim 1, wherein the lipo-chitooligosaccharide compound is
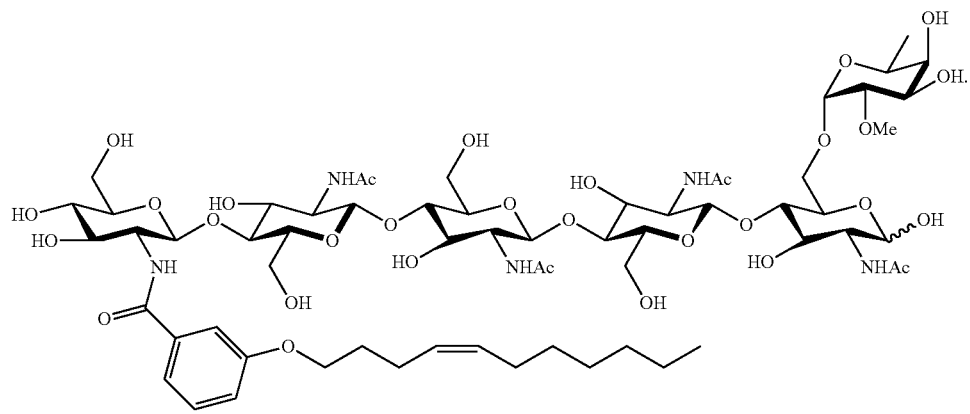
16. A composition according to claim 1, wherein the lipo-chitooligosaccharide compound is
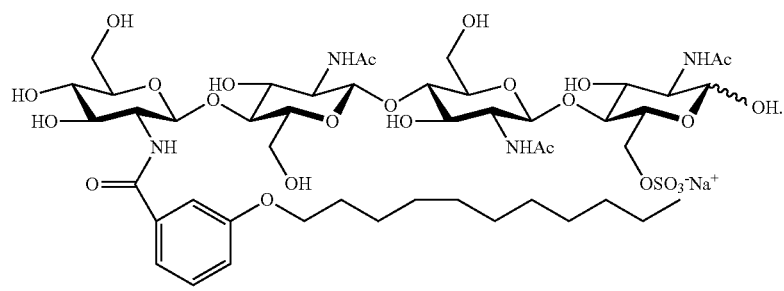
* * * * *